(12) United States Patent
Starke et al.

(10) Patent No.: US 7,132,416 B2
(45) Date of Patent: Nov. 7, 2006

(54) BENZOTHIAZEPINE AND BENZOTHIAZEPINE DERIVATIVES WITH ILEAL BILE ACID TRANSPORT (IBAT) INHIBOTORY ACTIVITY FOR THE TREATMENT HYPERLIPIDAEMIA

(75) Inventors: Ingemar Starke, Molndal (SE); Mikael Ulf Johan Dahlstrom, Molndal (SE); David Blomberg, Molndal (SE); Suzanne Alenfalk, Molndal (SE); Tore Skjaret, Molndal (SE); Malin Lemurell, Molndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/488,870

(22) PCT Filed: Sep. 5, 2002

(86) PCT No.: PCT/GB02/04033

§ 371 (c)(1),
(2), (4) Date: Oct. 7, 2004

(87) PCT Pub. No.: WO03/022286

PCT Pub. Date: Mar. 20, 2003

(65) Prior Publication Data

US 2005/0038009 A1 Feb. 17, 2005

(30) Foreign Application Priority Data

Sep. 8, 2001 (GB) .................................. 0121768.6
Apr. 25, 2002 (GB) .................................. 0209463.9

(51) Int. Cl.
C07D 281/02 (2006.01)
A61K 38/05 (2006.01)
A61K 38/06 (2006.01)

(52) U.S. Cl. ............................ 514/211.08; 514/211.09; 540/545; 540/552

(58) Field of Classification Search ........... 514/211.08, 514/211.09; 540/545, 552
See application file for complete search history.

(56) References Cited

U.S. PATENT DOCUMENTS

2002/0142054 A1  10/2002  Marlett et al.

FOREIGN PATENT DOCUMENTS

| | | |
|---|---|---|
| DE | 19825804 | 12/1999 |
| EP | 0372542 A | 6/1990 |
| EP | 0 864 582 | 9/1998 |
| GB | 2262888 | 7/1993 |
| WO | 93/16055 | 8/1993 |
| WO | 94/18183 | 8/1994 |
| WO | 94/18184 | 8/1994 |
| WO | 96/05188 | 2/1996 |
| WO | 96/08484 | 3/1996 |
| WO | 96/16051 | 5/1996 |
| WO | 97/33882 | 9/1997 |
| WO | 98/38182 A | 9/1998 |
| WO | 98/40375 | 9/1998 |
| WO | 99/01149 | 1/1999 |
| WO | 99/32478 | 7/1999 |
| WO | 99/35135 | 7/1999 |
| WO | 99/64409 | 12/1999 |
| WO | 99/64410 | 12/1999 |
| WO | 00/01687 | 1/2000 |
| WO | 00/38725 | 7/2000 |
| WO | 00/38726 | 7/2000 |
| WO | 00/38727 | 7/2000 |
| WO | 00/38728 | 7/2000 |
| WO | 00/38729 | 7/2000 |
| WO | 00/47568 A | 8/2000 |
| WO | 00/61568 | 10/2000 |
| WO | 00/62810 | 10/2000 |
| WO | 01/60807 A1 | 8/2001 |
| WO | 01/66533 A | 9/2001 |
| WO | 01/68096 A2 | 9/2001 |
| WO | 01/68637 A2 | 9/2001 |
| WO | 02/08211 A2 | 1/2002 |
| WO | 02/32428 A2 | 4/2002 |

(Continued)

OTHER PUBLICATIONS

Govers et al., Journal of Lipid Research, 35(5), 1994, pp. 741-748.

(Continued)

Primary Examiner—Bruck Kifle
(74) Attorney, Agent, or Firm—Morgan Lewis & Bockius LLP

(57) ABSTRACT

The present invention relates to compounds of formula (I) wherein $R^v$, $R^1$, $R^2$, $R^x$, $R^y$, M, $R^z$, v, $R^3$, $R^4$, $R^5$ and $R^6$ are as defined within; pharmaceutically acceptable salts, solvates, solvates of such salts and prodrugs thereof and their use as ileal bile acid transport (IBAT) inhibitors for the treatment of hyperlipidaemia. Processes for their manufacture and pharmaceutical compositions containing them are also described.

(I)

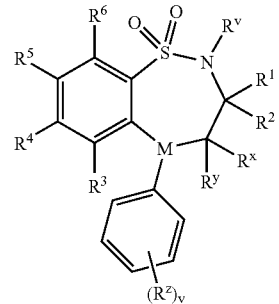

15 Claims, No Drawings

FOREIGN PATENT DOCUMENTS

| WO | 02/50051 A | 6/2002 |
| WO | 02/053548 A1 | 7/2002 |
| WO | 03/020710 A1 | 3/2003 |
| WO | 03/022825 A1 | 3/2003 |
| WO | 03/022830 A1 | 3/2003 |
| WO | 03/061663 A1 | 7/2003 |
| WO | 03/091232 A2 | 11/2003 |
| WO | 03/106482 A2 | 12/2003 |
| WO | 2004/006899 A1 | 1/2004 |
| WO | 2004/076430 A1 | 9/2004 |
| WO | 2004/089350 A1 | 10/2004 |

OTHER PUBLICATIONS

Higaki et al., Arteriosclerosis, Thombosis, and Vascular Biology, 18(8), 1998, pp. 1304-1311.

Ishibashi et al., Journal of Clinical Investigation, 92(2), 1993, pp. 883-893.

Lewis et al., Journal of Lipid Research, 36, 1995, pp. 1098-1105.

Plump et al., Cell, (71), 1992, pp. 343-353.

Schiller, Alimentary Pharmacology and Therapeutics, 15(6), 2001, pp. 749-763.

Sprong et al., J. Nutrition (US), 132(6), 2002, pp. 1269-1274.

Van Tilburg et al., Gastroenterology, 98(1), 1989, pp. 25-32.

Welberg et al., Scandinavian J. Gastroenterology Suppl Norway, 188, 1991, pp. 52-59.

BENZOTHIAZEPINE AND BENZOTHIAZEPINE DERIVATIVES WITH ILEAL BILE ACID TRANSPORT (IBAT) INHIBOTORY ACTIVITY FOR THE TREATMENT HYPERLIPIDAEMIA

This application is a 371 of PCT/GB02/04033, filed Sep. 5, 2002.

This invention relates to benzothiazepine and benzothiadiazepine derivatives, or pharmaceutically acceptable salts, solvates, solvates of such salts and prodrugs thereof. These benzothiazepines and benzothiadiazepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiazepine and benzothiadiazepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930–1938 and "Diabetes and Cardiovascular Disease: A Statement for Healthcare Professionals from the American Heart Association" Grundy S, Benjamin I., Burke G., et al; Circulation, 1999, 100, 1134–46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269–74) involved the treatment with substances with an IBAT inhibitory effect.

Re-absorption of bile acid from the gastrointestinal tract is a normal physiological process which mainly takes place in the ileum by the IBAT mechanism. Inhibitors of IBAT can be used in the treatment of hypercholesterolaemia (see for instance "Interaction of bile acids and cholesterol with nonsystemic agents having hypocholesterolaemic properties", Biochemica et Biophysica Acta, 1210 (1994) 255–287). Thus, suitable compounds having such inhibitory IBAT activity are also usefull in the treatment of hyperlipidaemic conditions. Substituted compounds possessing such IBAT inhibitory activity have been described, see for instance hypolipidaemic compounds described in WO 93/16055, WO 94/18183, WO 94/18184, WO 96/05188, WO 96/08484, WO 96/16051, WO 97/33882, WO 98/38182, WO 99/35135, WO 98/40375, WO 99/35153, WO 99/64409, WO 99/64410, WO 00/01687, WO 00/47568, WO 00/61568, WO 01/68906, DE 19825804, WO 00/38725, WO 00/38726, WO 00/38727, WO 00/38728, WO 00/38729, WO 01/68906 and EP 0 864 582.

A further aspect of this invention relates to the use of the compounds of the invention in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In addition, these compounds are expected to be useful for the prevention and treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks.

The present invention is based on the discovery that certain benzothiazepine and benzothiadiazepine compounds surprisingly inhibit IBAT. Such properties are expected to be of value in the treatment of disease states associated with hyperlipidaemic conditions.

Accordingly, the present invention provides a compound of formula (I):

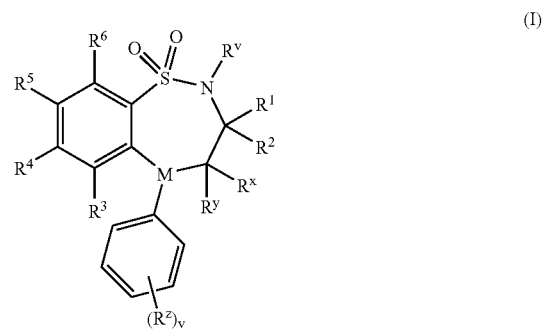

wherein:

$R^v$ is selected from hydrogen or $C_{1-6}$alkyl;

One of $R^1$ and $R^2$ are selected from hydrogen, $C_{1-6}$alkyl or $C_{2-6}$alkenyl and the other is selected from $C_{1-6}$alkyl or $C_{2-6}$alkenyl;

$R^x$ and $R^y$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

M is selected from —N— or —CH—;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$ alkyl)$_2$sulphamoyl;

v is 0–5;

one of $R^4$ and $R^5$ is a group of formula (IA):

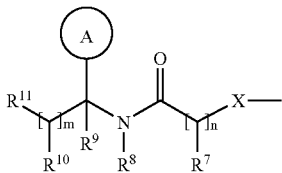

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$ alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (IB) or (IC):

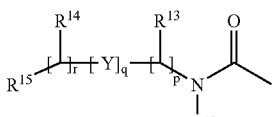

(IB)

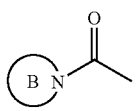

(IC)

wherein:

Y is —N(R'')—, —N(R'')C(O)—, —N(R'')C(O)(CR$^s$R$^t$)$_v$ N(R'')C(O)—, —O—, and —S(O)$_a$—; wherein a is 0–2, v is 1–2, R$^s$ and R$^t$ are independently selected from hydrogen or $C_{1-4}$alkyl optionally substituted by $R^{26}$ and R'' is hydrogen or $C_{1-4}$alkyl;

$R^{12}$ is hydrogen or $C_{1-4}$alkyl;

$R^{13}$ and $R^{14}$ are independently selected from hydrogen, $C_{1-6}$alkyl, carbocyclyl or heterocyclyl; and when q is 0, $R^{14}$ may additionally be selected from hydroxy; wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

Ring B is a nitrogen linked heterocyclyl substituted on carbon by one group selected from $R^{23}$, and optionally additionally substituted on carbon by one or more $R^{24}$; and wherein if said nitrogen linked heterocyclyl contains an —NH— moiety, that nitrogen may be optionally substituted by a group selected from $R^{25}$;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alklanoyloxy, N-($C_{1-4}$alkyl)amino, N,N-($C_{1-4}$alkyl)$_2$amnio, $C_{1-4}$alkanoylamino, N-($C_{1-4}$ alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{24}$ and $R^{26}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$aylkyl)$_2$amino, $C_{1-4}$alkanoylamino, N-($C_{1-4}$ alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, carbocyclyl, heterocyclyl, benzyloxycarbonylamino, ($C_{1-4}$ alkyl)$_3$silyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein $R^{19}$, $R^{20}$, $R^{24}$ and $R^{26}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{23}$ is carboxy, sulpho, sulphino, phosphono, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from $C_{1-6}$alkyl;

$R^{25}$ is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzyl, benzyloxycarbonyl, benzoyl and phenylsulphonyl;

or a pharmaceutically acceptable salt, solvate, solvate of such a salt or a prodrug thereof.

According to a further aspect of the present invention there is provided a compound of formula (I):

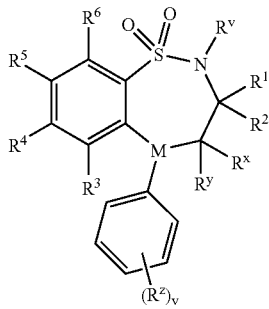

(I)

wherein:

R$^v$ is selected from hydrogen or C$_{1-6}$alkyl;

One of R$^1$ and R$^2$ are selected from hydrogen or C$_{1-6}$alkyl and the other is selected from C$_{1-6}$alkyl;

R$^x$ and R$^y$ are independently selected from hydrogen, hydroxy, amino, mercapto, C$_{1-6}$alkyl, C$_{1-6}$alkoxy, N-(C$_{1-6}$alkyl)amino, N,N-(C$_{1-6}$alkyl)$_2$amino, C$_{1-6}$alkylS(O)$_a$ wherein a is 0 to 2;

M is selected from —N— or —CH—;

R$^z$ is selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl and N,N-(C$_{1-6}$alkyl)$_2$sulphamoyl;

v is 0–5;

one of R$^4$ and R$^5$ is a group of formula (IA):

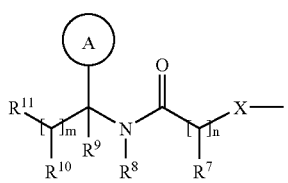

(IA)

R$^3$ and R$^6$ and the other of R$^4$ and R$^5$ are independently selected from hydrogen, halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, C$_{1-4}$alkanoylamino, N-(C$_{1-4}$alkyl)carbamoyl, N,N-(C$_{1-4}$alkyl)$_2$carbamoyl, C$_{1-4}$alkylS(O)$_a$ wherein a is 0 to 2, C$_{1-4}$alkoxycarbonyl, N-(C$_{1-4}$alkyl)sulphamoyl and N,N-(C$_{1-4}$ alkyl)$_2$sulphamoyl; wherein R$^3$ and R$^6$ and the other of R$^4$ and R$^5$ may be optionally substituted on carbon by one or more R$^{16}$;

X is —O—, —N(R$^a$)—, —S(O)$_b$— or —CH(R$^a$)—; wherein R$^a$ is hydrogen or C$_{1-6}$alkyl and b is 0–2;

Ring A is aryl or heteroaryl; wherein Ring A is optionally substituted by one or more substituents selected from R$^{17}$;

R$^7$ is hydrogen, C$_{1-4}$alkyl, carbocyclyl or heterocyclyl; wherein R$^7$ is optionally substituted by one or more substituents selected from R$^{18}$;

R$^8$ is hydrogen or C$_{1-4}$alkyl;

R$^9$ is hydrogen or C$_{1-4}$alkyl;

R$^{10}$ is hydrogen, C$_{1-4}$alkyl, carbocyclyl or heterocyclyl; wherein R$^{10}$ is optionally substituted by one or more substituents selected from R$^{19}$;

R$^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from C$_{1-6}$alkyl; or R$^{11}$ is a group of formula (IB):

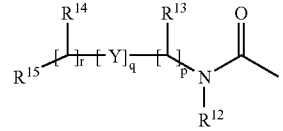

(IB)

wherein:

Y is —N(R″)—, —N(R″)C(O)—, —O—, and —S(O)$_a$; wherein a is 0–2 and R″ is hydrogen or C$_{1-4}$alkyl;

R$^{12}$ is hydrogen or C$_{1-4}$alkyl;

R$^{13}$ and R$^{14}$ are independently selected from hydrogen, C$_{1-4}$alkyl, carbocyclyl or heterocyclyl; wherein R$^{13}$ and R$^{14}$ may be independently optionally substituted by one or more substituents selected from R$^{20}$;

R$^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from C$_{1-6}$alkyl;

p is 1–3; wherein the values of R$^{13}$ maybe the same or different;

q is 0–1;

r is 0–3; wherein the values of R$^{14}$ may be the same or different;

m is 0–2; wherein the values of R$^{10}$ may be the same or different;

n is 1–3; wherein the values of R$^7$ may be the same or different;

R$^{16}$, R$^{17}$ and R$^{18}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, C$_{1-4}$alkanoylamino, N-(C$_{1-4}$alkyl)carbamoyl, N,N-(C$_{1-4}$alkyl)$_2$carbamoyl, C$_{1-4}$alkylS(O)$_a$, wherein a is 0 to 2, C$_{1-4}$alkoxycarbonyl, N-(C$_{1-4}$alkyl)sulphamoyl and N,N-(C$_{1-4}$akyl)$_2$sulphamoyl; wherein R$^{16}$, R$^{17}$ and R$^{18}$ may be independently optionally substituted on carbon by one or more R$^{21}$;

R$^{19}$ and R$^{20}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, C$_{1-4}$alkanoylamino, N-(C$_{1-4}$alkyl)carbamoyl, N,N-(C$_{1-4}$alkyl)$_2$carbamoyl, C$_{1-4}$alkylS(O)$_a$ wherein a is 0 to 2, C$_{1-4}$alkoxycarbonyl, N-(C$_{1-4}$alkyl)sulphamoyl, N,N-(C$_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from C$_{1-6}$alkyl; wherein R$^{19}$ and R$^{20}$ may be independently optionally substituted on carbon by one or more R$^{22}$;

R$^{21}$ and R$^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

According to a further aspect of the present invention there is provided a compound of formula (I):

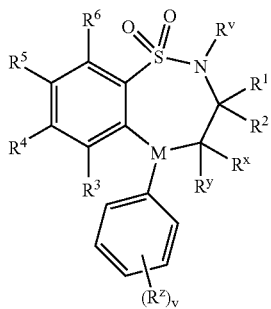

(I)

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

M is selected from —N— or —CH—;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0–5;

one of $R^4$ and $R^5$ is a group of formula (IA):

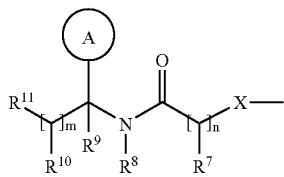

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$ alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (IB) or (IC):

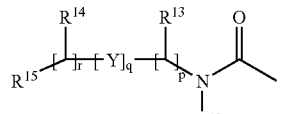

(IB)

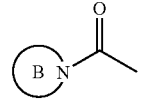

(IC)

wherein:

Y is —N(R″)—, —N(R″)C(O)—, —N(R″)C(O)(CR$^s$R$^t$)$_v$N(R″)C(O)—, —O—, and —S(O)a—; wherein a is 0–2, v is 1–2, R$^s$ and R$^t$ are independently selected from hydrogen or $C_{1-4}$alkyl optionally substituted by $R^{26}$ and R″ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; and when q is 0, $R^{14}$ may additionally be selected from hydroxy; wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

Ring B is a nitrogen linked heterocyclyl substituted on carbon by one group selected from $R^{23}$, and optionally additionally substituted on carbon by one or more $R^{24}$; and wherein if said nitrogen linked heterocyclyl contains an —NH— moiety, that nitrogen may be optionally substituted by a group selected from $R^{25}$;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)

amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{24}$ and $R^{26}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl) amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, carbocyclyl, heterocyclyl, benzyloxycarbonylamino, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein $R^a$ and $R^b$ are independently selected from $C_{1-6}$alkyl; wherein $R^{19}$, $R^{20}$, $R^{24}$ and $R^{26}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{23}$ is carboxy, sulpho, sulphino, phosphono, —P(O)(OR$^g$)(OR$^h$), —P(O)(OH)(OR$^g$), —P(O)(OH)(R$^g$) or —P(O)(OR$^g$)(R$^h$) wherein $R^g$ and $R^h$ are independently selected from $C_{1-6}$alkyl;

$R^{25}$ is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzyl, benzyloxycarbonyl, benzoyl and phenylsulphonyl;

or a pharmaceutically acceptable salt, solvate, solvate of such a salt or a prodrug thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-6}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3–12 atoms of which at least one atom is chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. Examples and suitable values of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl.

"Aryl" is a totally unsaturated, mono or bicyclic carbon ring that contains 3–12 atoms. Preferably "aryl" is a monocyclic ring containing 5 or 6 atoms or a bicyclic ring containing 9 or 10 atoms. Suitable values for "aryl" include phenyl or naphthyl. Particularly "aryl" is phenyl.

A "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl pyranyl, indolyl, pyrrimdyl, thiazolyl, pyrazinyl, pyridazinyl, pyridyl, 4-pyridonyl, quinolyl and 1-isoquinolonyl.

A "nitrogen linked heterocyclyl" is a saturated, partially saturated or unsaturated, mono or bicyclic ring containing 3–12 atoms of which at least one atom is nitrogen and the heterocyclyl is linked to the carbonyl group of formula (IC) via this nitrogen, which may additionally contain further heteroatoms chosen from nitrogen, sulphur or oxygen, wherein a —CH$_2$— group can optionally be replaced by a —C(O)— or a ring sulphur atom may be optionally oxidised to form the S-oxides. Preferably a "nitrogen linked heterocyclyl" is a saturated, partially saturated or unsaturated, mono or bicyclic ring containing 5 or 6 atoms of which at least one atom is nitrogen and the heterocyclyl is linked to the carbonyl group of formula (IC) via this nitrogen, which may additionally contain further heteroatoms chosen from nitrogen, sulphur or oxygen, wherein a —CH$_2$— group can optionally be replaced by a —C(O)— or a ring sulphur atom may be optionally oxidised to form the S-oxides. Examples and suitable values of the term "nitrogen linked heterocyclyl" are morpholino, pyrrolidin-1-yl, imidazol-1-yl, pyrazolidin-1-yl, piperidin-1-yl and piperazin-1-yl. Particularly a "nitrogen linked heterocyclyl" is pyrrolidin-1-yl.

A "carbocyclyl" is a saturated, partially saturated or unsaturated, mono or bicyclic carbon ring that contains 3–12 atoms; wherein a —CH$_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$alkanoyloxy" and "$C_{1-4}$alkanoyloxy" is acetoxy. Examples of "$C_{1-6}$alkoxycarbonyl" and "$C_{1-4}$alkoxycarbonyl" include methoxycarbonyl, ethoxycarbonyl, n- and t-butoxycarbonyl. Examples of "$C_{1-6}$alkoxy" and "$C_{1-4}$alkoxy" include methoxy, ethoxy and propoxy. Examples of "$C_{1-6}$alkanoylamino" and "$C_{1-4}$alkanoylamino" include formamido, acetamido and propionylamino. Examples of "$C_{1-6}$alkylS(O)$_a$ wherein a is 0 to 2" and "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl" and "$C_{1-4}$alkanoyl" include propionyl and acetyl. Examples of "N-($C_{1-6}$alkyl)amino" and "N-($C_{1-4}$alkyl)amino" include methylamino and ethylamino. Examples of "N,N-($C_{1-6}$alkyl)$_2$amino" and "N,N-($C_{1-4}$alkyl)$_2$amino" include di-N-methylamino, di-(N-ethyl)amino and N-ethyl-N-methylamino. Examples of "$C_{2-6}$ alkenyl" and "$C_{2-4}$alkenyl" are vinyl, allyl and 1-propenyl. Examples of "$C_{2-6}$alkynyl" and "$C_{2-4}$alkynyl" are ethynyl, 1-propynyl and 2-propynyl. Examples of "N-($C_{1-6}$alkyl)sulphamoyl" and "N-($C_{1-4}$alkyl)sulphamoyl" are N-($C_{1-3}$alkyl)sulphamoyl, N-(methyl)sulphamoyl and N-(ethyl)sulphamoyl. Examples of "N-($C_{1-6}$alkyl)$_2$sulphamoyl" "N-($C_{1-4}$alkyl)$_2$sulphamoyl" are N,N-(dimethyl)sulphamoyl and N-(methyl)-N-(ethyl)sulphamoyl. Examples of "N-($C_{1-6}$alkyl)carbamoyl" and "N-($C_{1-4}$alkyl)carbamoyl" are methylaminocarbonyl and ethylaminocarbonyl. Examples of "N,N-($C_{1-6}$alkyl)$_2$carbamoyl" and "N,N-($C_{1-4}$alkyl)$_2$carbamoyl" are dimethylaminocarbonyl and methylethylaminocarbonyl. Example of "$C_{1-6}$alkylsulphonyl" are mesyl and ethylsulphonyl. Examples of "($C_{1-4}$alkyl)$_3$silyl," include trimethylsilyl and methyldiethylsilyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetic or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N-$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Particular values are as follows. Such values maybe used where appropriate with any of the definitions, claims or embodiments defined hereinbefore or hereinafter.

$R^v$ is hydrogen.
$R^1$ and $R^2$ are $C_{1-4}$alkyl.
$R^1$ and $R^2$ are both butyl.
One of $R^1$ and $R^2$ is ethyl and the other is butyl.
One of $R^x$ and $R^y$ is hydrogen and the other is hydroxy.
$R^x$ and $R^y$ are both hydrogen.
M is —N—.
M is —CH—.
v is 0 or 1.
v is 0.
$R^z$ is $C_{1-4}$alkyl.
$R^3$ and $R^6$ are hydrogen.
$R^4$ is methylthio or bromo.
$R^4$ is methylthio.
$R^4$ is halo, $C_{1-4}$alkyl or $C_{1-4}$alkylS(O)$_a$ wherein a is 0.
$R^4$ is bromo, methyl or methylthio.
$R^5$ is a group of formula (IA) (as depicted above) wherein:
X is —O—;
Ring A is phenyl optionally substituted by one or more substituents selected from $R^{17}$;
n is 1;
$R^7$ is hydrogen;
$R^8$ is hydrogen;
$R^9$ is hydrogen;
m is 0;

R¹¹ is a group of formula (IB) (as depicted above) wherein:
R¹² is hydrogen;
p is 1 or 2;
R¹³ is hydrogen;
q is 0;
r is 0;
R¹⁵ is carboxy or sulpho; and
R¹⁷ is hydroxy.
R⁵ is N-{(R)-α-[N-(carboxymethyl)carbamoyl]benzyl}carbamoylmethoxy, or N-{(R)-α-[N-(2-sulphoethyl)carbamoyl]-4-hydroxybenzyl}carbamoylmethoxy.
R⁵ is a group of formula (IA) (as depicted above) wherein:
X is —O—;
Ring A is phenyl optionally substituted by one or more substituents selected from R¹⁷;
n is 1;
R⁷ is hydrogen;
R⁸ is hydrogen;
R⁹ is hydrogen;
m is 0;
R¹¹ is carboxy, a group of formula (IB) (as depicted above) or a group of formula (IC) (as depicted above) wherein:
R¹² is hydrogen or C₁₋₄alkyl;
p is 1 or 2;
R¹³ is hydrogen or C₁₋₄alkyl optionally substituted by R²⁰ wherein R²⁰ is hydroxy, carbamoyl, amino, benzyloxycarbonylamino or C₁₋₄alkylS(O)ₐ wherein a is 0;
R¹⁴ is hydrogen or hydroxy;
q is 0;
r is 0 or 1;
R¹⁵ is carboxy or sulpho;
R¹⁷ is hydroxy; and
Ring B is pyrrolidin-1-yl substituted on carbon by one group selected from R²³; wherein R²³ is carboxy.
R⁵ is N-{(R)-α-[N-(carboxymethyl)carbamoyl]benzyl}carbamoylmethoxy, N-{(R)-α-[N-(2-sulphoethyl)carbamoyl]-4-hydroxybenzyl}carbamoylmethoxy, N-{(R)-α-[N-((S)-1-carboxy-2-hydroxyethyl)carbamoyl]benzyl}carbamoylmethoxy, N-{(R)-α-[N-((S)-1-carboxyethyl)carbamoyl]benzyl}carbamoylmethoxy, N-{(R)-α-[N-((S)-1-carboxypropyl)carbamoyl]benzyl}carbamoylmethoxy, N-{(R)-α-[N-((R)-1-carboxy-2-methylthio-ethyl)carbamoyl]benzyl}carbamoylmethoxy, N-{(R)-α-[N-((S)-1-carboxy-2-carbamoylethyl)-carbamoyl]benzyl}carbamoylmethoxy, N-{(R)-α-[N-(2-sulphoethyl)carbamoyl]-4-hydroxybenzyl}carbamoylmethoxy, N-{(R)-α-[N-(carboxymethyl)carbamoyl]-4-hydroxybenzyl}carbamoylmethoxy, N-{(R)-α-[N-((S)-1-carboxyethyl)carbamoyl]-4-hydroxybenzyl}carbamoylmethoxy, N-{(R)-α-[N-((S)-1-carboxy-2-hydroxyethyl)carbamoyl]-4-hydroxybenzyl}carbamoylmethoxy, N-{(R)-α-[N-(2-sulphoethyl)carbamoyl]benzyl}carbamoylmethoxy, N-{(R)-α-[N-((S)-1-carboxy-2-(R)-hydroxypropyl)carbamoyl]benzyl}carbamoylmethoxy, N-{(R)-α-[N-((S)-1-carboxy-2-methylpropyl)carbamoyl]benzyl}carbamoylmethoxy, N-{(R)-α-[N-((S)-1-carboxy-3-methylbutyl)carbamoyl]benzyl}carbamoylmethoxy, N-{(R)-α-[N-(1-(S)-1-carboxy-2-(S)-2-methylbutyl)carbamoyl]benzyl}carbamoylmethoxy, N-((R)-α-carboxy-4-hydroxybenzyl)carbamoylmethoxy, N-{(R)-α-[N-((S)-1-carboxy-4-aminobutyl)carbamoyl]benzyl}carbamoylmethoxy, N-((R)-α-{N-[(S)-1-carboxy-4-(benzyloxycarbonylamino)butyl]carbamoyl}benzyl)carbamoylmethoxy, N-[(R)-α-((S)-2-carboxypyrrolidin-1-ylcarbonyl)benzyl]carbamoylmethoxy, N-{(R)-α-[N-(carboxymethyl)-N-methylcarbamoyl]benzyl}carbamoylmethoxy, N-{(R)-α-[N-(1-(R)-2-(R)-1-carboxy-1-hydroxyprop-2-yl)carbamoyl]benzyl}carbamoylmethoxy, N-{(R)-α-[N-(sulphomethyl)carbamoyl]benzyl}carbamoylmethoxy, N-((R)-α-carboxybenzyl)carbamoylmethoxy, N-{(R)-α-[N-((S)-1-carboxy-2-(R)-hydroxypropyl)carbamoyl]-4-hydroxybenzyl}carbamoylmethoxy, N-{(R)-α-[N-((S)-1-carboxy-2-methylpropyl)carbamoyl]-4-hydroxybenzyl}carbamoylmethoxy, N-{(R)-α-[N-((S)-1-carboxybutyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy or N-{(R)-α-[N-((R)-1-carboxy-2-methylthio-ethyl)carbamoyl]-4-hydroxybenzyl}carbamoylmethoxy.
R⁵ is a group of formula (IA) (as depicted above) wherein:
X is —O—;
Ring A is phenyl optionally substituted by one or more substituents selected from R¹⁷;
n is 1;
R⁷ is hydrogen;
R⁸ is hydrogen;
R⁹ is hydrogen;
m is 0;
R¹¹ is carboxy, a group of formula (IB) (as depicted above) or a group of formula (IC) (as depicted above) wherein:
R¹² is hydrogen or C₁₋₄alkyl;
p is 1 or 2;
R¹³ is hydrogen or C₁₋₆alkyl optionally substituted by R²⁰ wherein R²⁰ is hydroxy, carbamoyl, amino, benzyloxycarbonylamino, C₁₋₄alkylS(O)ₐ wherein a is 0 or (C₁₋₄alkyl)₃silyl;
R¹⁴ is hydrogen or hydroxy or C₁₋₆alkyl; wherein R¹⁴ may be optionally substituted by one or more substituents selected from R²⁰;
Y is —N(R″)C(O)— wherein R″ is hydrogen;
q is 0 or 1;
r is 0 or 1;
R¹⁵ is carboxy or sulpho;
R¹⁷ is hydroxy; and
R²⁰ is selected from hydroxy;
Ring B is pyrrolidin-1-yl or azetidinyl substituted on carbon by one group selected from R²³, and optionally additionally substituted on carbon by one or more R²⁴; wherein R²³ is carboxy and R²⁴ is hydroxy.
R⁵ is N-{(R)-α-[N-(carboxymethyl)carbamoyl]benzyl}carbamoylmethoxy, N-{(R)-α-[N-(2-sulphoethyl)carbamoyl]-4-hydroxybenzyl}carbamoylmethoxy, N-{(R)-α-[N-((S)-1-carboxy-2-hydroxyethyl)carbamoyl]benzyl}carbamoylmethoxy, N-{(R)-α-[N-((S)-1-carboxyethyl)carbamoyl]benzyl}carbamoylmethoxy, N-{(R)-α-[N-((S)-1-carboxypropyl)carbamoyl]benzyl}carbamoylmethoxy, N-{(R)-α-[N-((R)-1-carboxy-2-methylthio-ethyl)carbamoyl]benzyl}carbamoylmethoxy, N-{(R)-α-[N-((S)-1-carboxy-2-carbamoyl-ethyl)carbamoyl]benzyl}carbamoylmethoxy, N-{(R)-α-[N-(2-sulphoethyl)carbamoyl]-4-hydroxybenzyl}carbamoylmethoxy, N-{(R)-α-[N-(carboxymethyl)carbamoyl]-4-hydroxybenzyl}carbamoylmethoxy, N-({(R)-α-[N-((S)-1-carboxyethyl)carbamoyl]-4-hydroxybenzyl}carbamoylmethoxy, N-{(R)-α-[N-((S)-1-carboxy-2-hydroxyethyl)carbamoyl]-4-hydroxybenzyl}carbamoylmethoxy, N-{(R)-α-[N-(2-sulphoethyl)carbamoyl]benzyl}carbamoylmethoxy, N-{(R)-α-[N-((S)-1-carboxy-2-(R)-hydroxypropyl)carbamoyl]benzyl}carbamoylmethoxy, N-{(R)-α-[N-((S)-1-carboxy-2-methylpropyl)carbamoyl]benzyl}carbamoylmethoxy, N-{(R)-α-[N-((S)-1-carboxy-3-methylbutyl)carbamoyl]benzyl}carbamoylmethoxy, N-{(R)-α-[N-(1-(S)-1-carboxy-2-(S)-2-methylbutyl)carbamoyl]benzyl}carbamoylmethoxy, N-((R)-α-carboxy-4-hydroxybenzyl)carbamoylmethoxy, N-{(R)-α-[N-((S)-1-carboxy-4-aminobutyl)carbamoyl] benzyl}carbamoylmethoxy, N-((R)-α-{N-[(S)-1-carboxy-4-(benzyloxycarbonylamino)butyl]carbamoyl}benzyl)carbamoylmethoxy, N-[(R)-α-((S)-2-carboxypyrrolidin-1-ylcarbonyl)benzyl]carbamoylmethoxy, N-{()-α-[N-(carboxymethyl)-N-methylcarbamoyl] benzyl}carbamoylmethoxy, N-{(R)-α-[N-(1-(R)-2-(R)-1-carboxy-1-hydroxyprop-2-yl)carbamoyl] benzyl}carbamoylmethoxy, N-{(R)-α-[N-(sulphomethyl) carbamoyl]benzyl}carbamoylmethoxy, N-((R)-α-carboxybenzyl)carbamoylmethoxy, N-{(R)-α-[N-((S)-1-carboxy-2-(R)-hydroxypropyl)carbamoyl]-4-hydroxybenzyl}carbamoylmethoxy, N-{(R)-α-[N-((S)-1-carboxy-2-methylpropyl)carbamoyl]-4-hydroxybenzyl}carbamoylmethoxy, N-{(R)-α-[N-((S)-1-carboxybutyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-((R)-1-carboxy-2methylthio-ethyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-{(S)-1-[N-((S)-2-hydroxy-1-carboxyethyl)carbamoyl] propyl}carbamoyl]benzyl}carbamoylmethoxy, N-{(R)-α-[2-(S)-2-(carboxy)-4-(R)-4-(hydroxy)pyrrolidin-1-ylcarbonyl]benzyl}carbamoylmethoxy, N-{(R)-α-[2-(S)-2-(carboxy)azetidin-1-ylcarbonyl]benzyl}carbamoylmethoxy, N-{(R)-α-[N-{(S)-1-[N-((S)-1-carboxyethyl)carbamoyl] ethyl}carbamoyl]benzyl}carbamoylmethoxy, N-{(R)-α-[N-(R)-1-carboxy-3,3-dimethylbutyl)carbamoyl] benzyl}carbamoylmethoxy, N-{(R)-α-[N-((S)-1-carboxy-3,3-dimethylbutyl)carbamoyl]benzyl}carbamoylmethoxy, N-{(R)-α-[N-((R)-1-carboxy-3,3-dimethylbutyl)carbamoyl}-4-hydroxybenzyl}carbamoylmethoxy, N-((R)-α-{(N-[(S)-1-carboxy-2-(trimethylsilyl)ethyl]carbamoyl}-4-hydroxybenzyl)carbamoylmethoxy or N-((R)-α-{N-[(R)-1-carboxy-2-(trimethylsilyl)ethyl]carbamoyl}-4hydroxybenzyl)carbamoylmethoxy.

$R^5$ is hydrogen.
$R^4$ is a group of formula (IA).
$R^5$ is a group of formula (IA).

Therefore in an further aspect of the invention, there is provided a compound of formula (I) (as depicted above) wherein:

$R^v$ is hydrogen;
$R^1$ and $R^2$ are $C_{1-4}$alkyl;
$R^x$ and $R^y$ are both hydrogen;
M is —N—;
v is 0;
$R^3$ and $R^6$ are hydrogen;
$R^4$ is halo, $C_{1-4}$alkyl or $C_{1-4}$alkylS(O)$_a$ wherein a is 0;
$R^5$ is a group of formula (IA) (as depicted above) wherein:
X is —O—;
Ring A is phenyl optionally substituted by one or more substituents selected from $R^{17}$;
n is 1;
$R^7$ is hydrogen;
$R^8$ is hydrogen;
$R^9$ is hydrogen;
m is 0;
$R^{11}$ is carboxy, a group of formula (IB) (as depicted above) or a group of formula (IC) (as depicted above) wherein:
$R^{12}$ is hydrogen or $C_{1-4}$alkyl;
p is 1 or 2;
$R^{13}$ is hydrogen or $C_{1-6}$alkyl optionally substituted by $R^{20}$ wherein $R^{20}$ is hydroxy, carbamoyl, amino, benzyloxycarbonylamino, $C_{1-4}$alkylS(O)$_a$ wherein a is 0 or $(C_{1-4}$alkyl)$_3$silyl;

$R^{14}$ is hydrogen or hydroxy or $C_{1-6}$alkyl; wherein $R^{14}$ may be optionally substituted by one or more substituents selected from $R^{20}$;
Y is —N(R″)C(O)— wherein R″ is hydrogen;
q is 0 or 1;
r is 0 or 1;
$R^{15}$ is carboxy or sulpho;
$R^{17}$ is hydroxy; and
$R^{20}$ is selected from hydroxy; and
Ring B is pyrrolidin-1-yl or azetidinyl substituted on carbon by one group selected from $R^{23}$, and optionally additionally substituted on carbon by one or more $R^{24}$; wherein $R^{23}$ is carboxy and $R^{24}$ is hydroxy; or a pharmaceutically acceptable salt, solvate, solvate of such a salt or a prodrug thereof.

Therefore in an additional aspect of the invention, there is provided a compound of formula (I) (as depicted above) wherein:

$R^v$ is hydrogen;
$R^1$ and $R^2$ are both butyl;
$R^x$ and $R^y$ are both hydrogen;
M is —N—;
v is 0;
$R^3$ and $R^6$ are hydrogen;
$R^4$ is bromo, methyl or methylthio; and
$R^5$ is N-{(R)-α-[N-(carboxymethyl)carbamoyl] benyzl}carbamoylmethoxy, N-(R)-α-[N-(2-sulphoethyl) carbamoyl]-4-hydroxybenzyl}carbamoylmethoxy, N-{(R)-α-[N-((S)-1-carboxy-2-hydroxyethyl)carbamoyl] benzyl}carbamoylmethoxy, N-{(R)-α-[N-((S)-1-carboxyethyl)carbamoyl]benzyl}carbamoylmethoxy, N-{(R)-α-[N-((S)-1-carboxypropyl)carbamoyl] benzyl}carbamoylmethoxy, N-{(R)-α-[N-(R)-1-carboxy-2-methylthio-ethyl)carbamoyl]benzyl}carbamoylmethoxy, N-{(R)-α-[N-((S)-1-carboxy-2-carbamoyl-ethyl)carbamoyl]benzyl}carbamoylmethoxy, N-{(R)-α-[N-(2-sulphoethyl)carbamoyl]4-hydroxybenzyl}carbamoylmethoxy, N-{(R)-α-[N-(carboxymethyl)carbamoyl]-4-hydroxybenzyl}carbamoylmethoxy, N-{(R)-α-[N-((S)-1-carboxyethyl)carbamoyl]-4-hydroxybenzyl}carbamoylmethoxy, N-{(R)-α-[N-((S)-1-carboxy-2-hydroxyethyl)carbamoyl]-4-hydroxybenzyl}carbamoylmethoxy, N-{(R)-α-[N-(2-sulphoethyl)carbamoyl)]benzyl}carbamoylmethoxy, N-{(R)-α-[N-((S)-1-carboxy-2-(R)-hydroxypropyl)carbamoyl] benzyl}carbamoylmethoxy, N-{(R)-α-[N-((S)-1-carboxy-2-methylpropyl)carbamoyl]benzyl}carbamoylmethoxy, N-{(R)-α-[N-((S)-1-carboxy-3-methylbutyl)carbamoyl] benzyl}carbamoylmethoxy, N-{(R)-α-[N-(1-(S)-1-carboxy-2-(S)-2-methylbutyl)carbamoyl]benzyl}carbamoylmethoxy, N-((R)-α-carboxy-4-hydroxybenzyl)carbamoylmethoxy, N-{(R)-α-[N-((S)-1-carboxy-4-aminobutyl)carbamoyl] benzyl}carbamoylmethoxy, N-((R)-α-{N-[(S)-1-carboxy-4-(benzyloxycarbonylamino)butyl]carbamoyl}benzyl)carbamoylmethoxy, N-[(R)-α-((S)-2-carboxypyrrolidin-1-ylcarbonyl)benzyl]carbamoylmethoxy, N-{(R)-α-[N-(carboxymethyl)-N-methylcarbamoyl] benzyl}carbamoylmethoxy, N-{(R)-α-[N-(1-(R)-2-(R)-1-carboxy-1-hydroxyprop-2-yl)carbamoyl] benzyl}carbamoylmethoxy, N-{(R)-α-[N-(sulphomethyl) carbamoyl]benzyl}carbamoylmethoxy, N-((R)-α-carboxybenzyl)carbamoylmethoxy, N-{(R)-α-[N-((S)-1-carboxy-2-(R)-hydroxypropyl)carbamoyl]-4-hydroxybenzyl}carbamoylmethoxy, N-{(R)-α-[N-((S)-1-carboxy-2-methylpropyl)carbamoyl]-4-hydroxybenzyl}carbamoylmethoxy, N-{(R)-α-[N-((S)-1-carboxybutyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-((R)-1- carboxy-2-methylthio-ethyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-{(S)-1-[N-((S)-2-hydroxy-1-carboxyethyl)carbamoyl]propyl]carbamoyl]benzyl}carbamoylmethoxy, N-{(R)-α-[2-(S)-2-(carboxy)-4-(R)-4-(hydroxy)pyrrolidin-1-ylcarbonyl]benzyl}carbamoylmethoxy, N-{(R)-α-[2-(S)-2-(carboxy)azetidin-1-ylcarbonyl]benzyl}carbamoylmethoxy, N-{(R)-α-[N-{(S)-1-[N-((S)-1-carboxyethyl)carbamoyl]ethyl}carbamoyl]benzyl}carbamoylmethoxy, N-{(R)-α-[N-(R)-1-carboxy-3,3-dimethylbutyl)carbamoyl]benzyl}carbamoylmethoxy, N-{(R)-α-[N-((S)-1-carboxy-3,3-dimethylbutyl)carbamoyl]benzyl}carbamoylmethoxy, N-{(R)-α-[N-((R)-1-carboxy-3,3-dimethylbutyl)carbamoyl]-4hydroxybenzyl}carbamoylmethoxy, N-((R)-α-{N-[(S)-1-carboxy-2-(trimethylsilyl)ethyl]carbamoyl}-4-hydroxybenzy)carbamoylmethoxy or N-((R)-α-{N-[(R)-1-carboxy-2-(trimethylsilyl)ethyl]carbamoyl}-4-hydroxybenzyl)carbamoylmethoxy;

or a pharmaceutically acceptable salt, solvate, solvate of such a salt or a prodrug thereof.

In another aspect of the invention, preferred compounds of the invention are any one of examples 5, 6, 7, 9, 11, 14, 15, 26, 27, 28, 30 or 33 or a pharmaceutically acceptable salt, solvate, solvate of such a salt or a prodrug thereof.

In another aspect of the invention, preferred compounds of the invention are any one of the examples or a pharmaceutically acceptable salt, solvate, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I) comprises of:

Process 1): for compounds of formula (I) wherein X is —O—, —NR$^a$ or —S—; reacting a compound of formula (IIa) or (IIb):

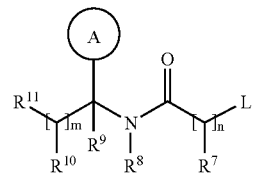
(IIa)

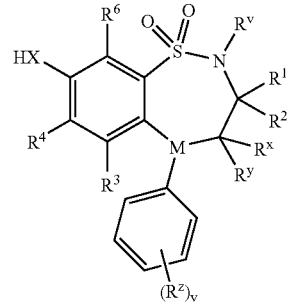
(IIb)

with a compound of formula (III):

(III)

wherein L is a displaceable group;

Process 2): reacting an acid of formula (IVa) or (IVb):

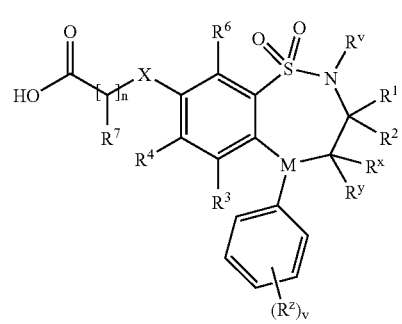
(IVa)

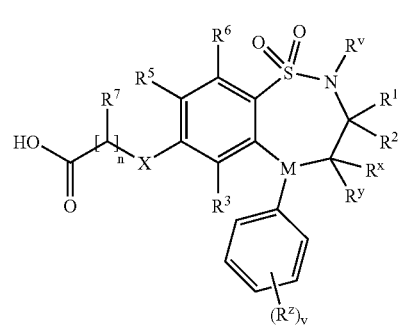
(IVb)

or an activated derivative thereof; with an amine of formula (V):

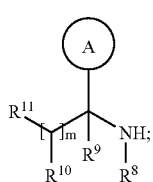
(V)

Process 3): for compounds of formula (I) wherein $R^{11}$ is a group of formula (IB); reacting a compound of formula (I) wherein $R^{11}$ is carboxy with an amine of formula (VI):

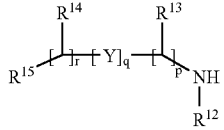
(VI)

Process 4) for compounds of formula (I) wherein one of $R^4$ and $R^5$ are independently selected from $C_{1-6}$alkylthio optionally substituted on carbon by one or more $R^{17}$; reacting a compound of formula (VIIa) or (VIIb):

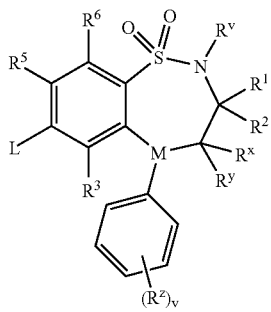
(VIIa)

(VIIb)

wherein L is a displaceable group; with a thiol of formula (VIII):

$$R^m\text{—}H \quad \text{(VIII)}$$

wherein $R^m$ is $C_{1-6}$alkylthio optionally substituted on carbon by one or more $R^{16}$;

Process 5): for compounds of formula (I) wherein $R^{11}$ is carboxy; deprotecting a compound of formula (IXa):

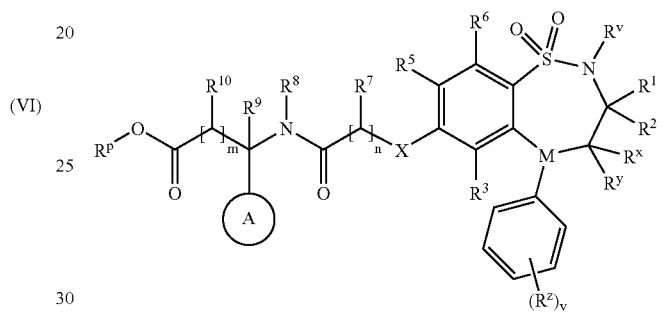
(IXa)

or (IXb):

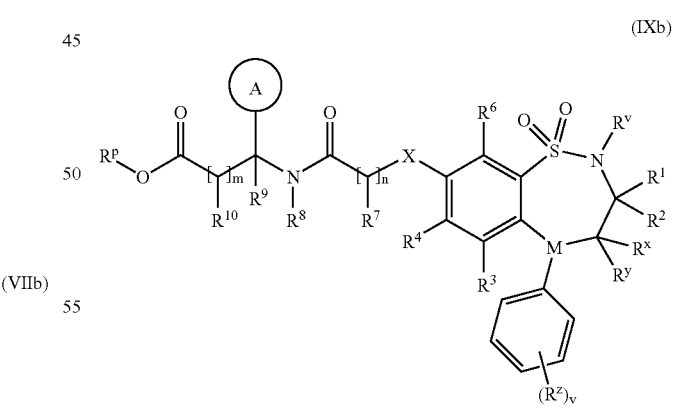
(IXb)

wherein $R^p$ together with the —OC(O)— group to which it is attached forms an ester;

Process 6): for compounds of formula (I) wherein $R^{11}$ is a group of formula (IB) and $R^{15}$ is carboxy; deprotecting a compound of formula (Xa):

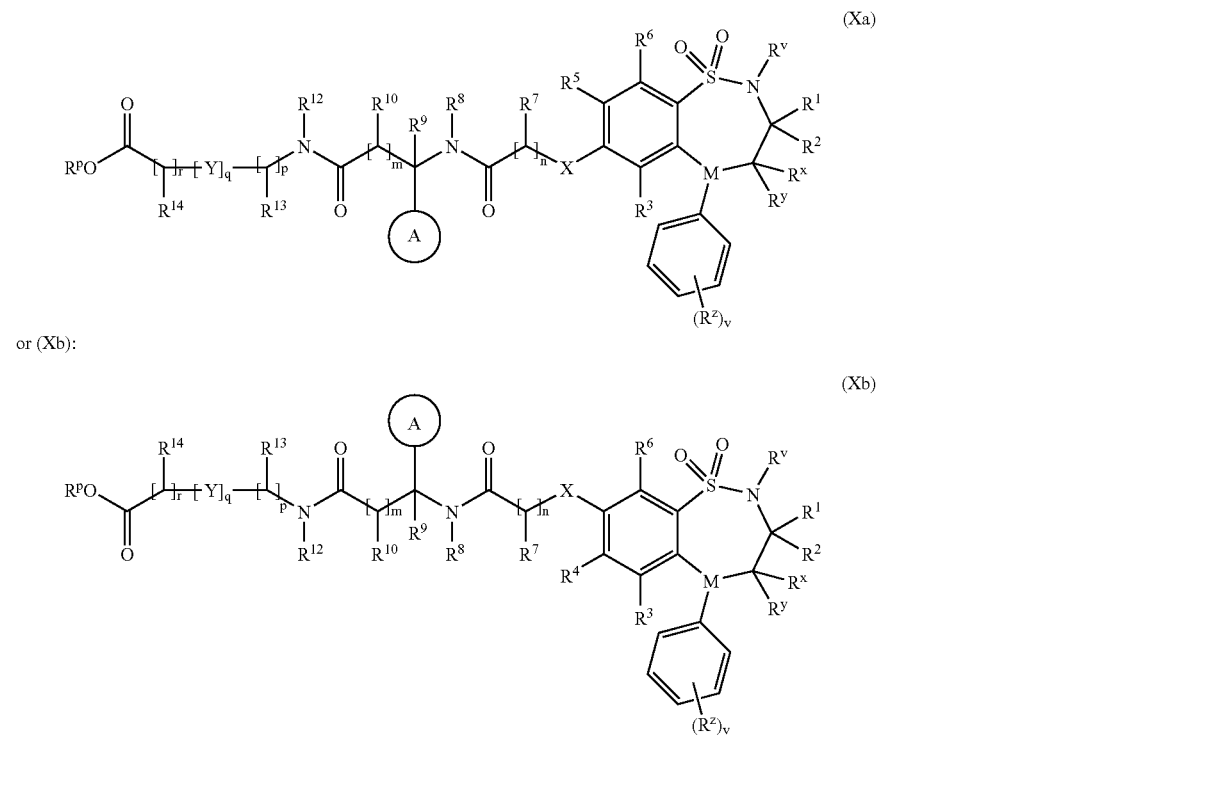

(Xa)

or (Xb):

(Xb)

wherein $R^p$ together with the —OC(O)— group to which it is attached forms an ester;

Process 7): for compounds of formula (I) wherein $R^{11}$ is a group of formula (IB) and $N(R'')C(O)$—; reacting an acid of formula (XIa):

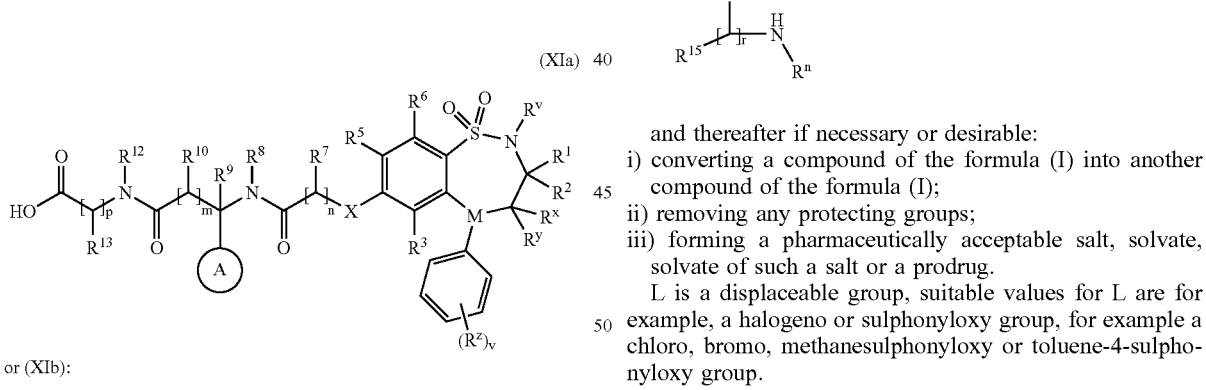

(XIa)

or (XIb):

(XIb)

or an activated derivative thereof; with an amine of formula (XII):

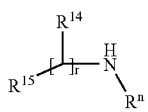

(XII)

and thereafter if necessary or desirable:
i) converting a compound of the formula (I) into another compound of the formula (I);
ii) removing any protecting groups;
iii) forming a pharmaceutically acceptable salt, solvate, solvate of such a salt or a prodrug.

L is a displaceable group, suitable values for L are for example, a halogeno or sulphonyloxy group, for example a chloro, bromo, methanesulphonyloxy or toluene-4-sulphonyloxy group.

$R^p$ together with the —OC(O)— group to which it is attached forms an ester. Preferably $R^p$ is methyl or ethyl. More preferably $R^p$ is methyl. In another aspect of the invention Rp is $C_{1-6}$alkyl or phenyl$C_{1-6}$alkyl, preferably $C_{1-4}$alkyl or benzyl, more preferably t-butyl, methyl, ethyl or benzyl.

Specific reaction conditions for the above reactions are as follows.

The bicyclic ring systems of the present invention may be assembled according to Scheme Ia or Scheme Ib. The skilled person will appreciate to make any of the above identified intermediates the value of $R^4$ or $R^5$ in the following schemes would be replaced with the appropriate group. For example, to synthesize a compound of formula (IIa) $R^4$ would be HX in the following scheme.

Scheme 1a
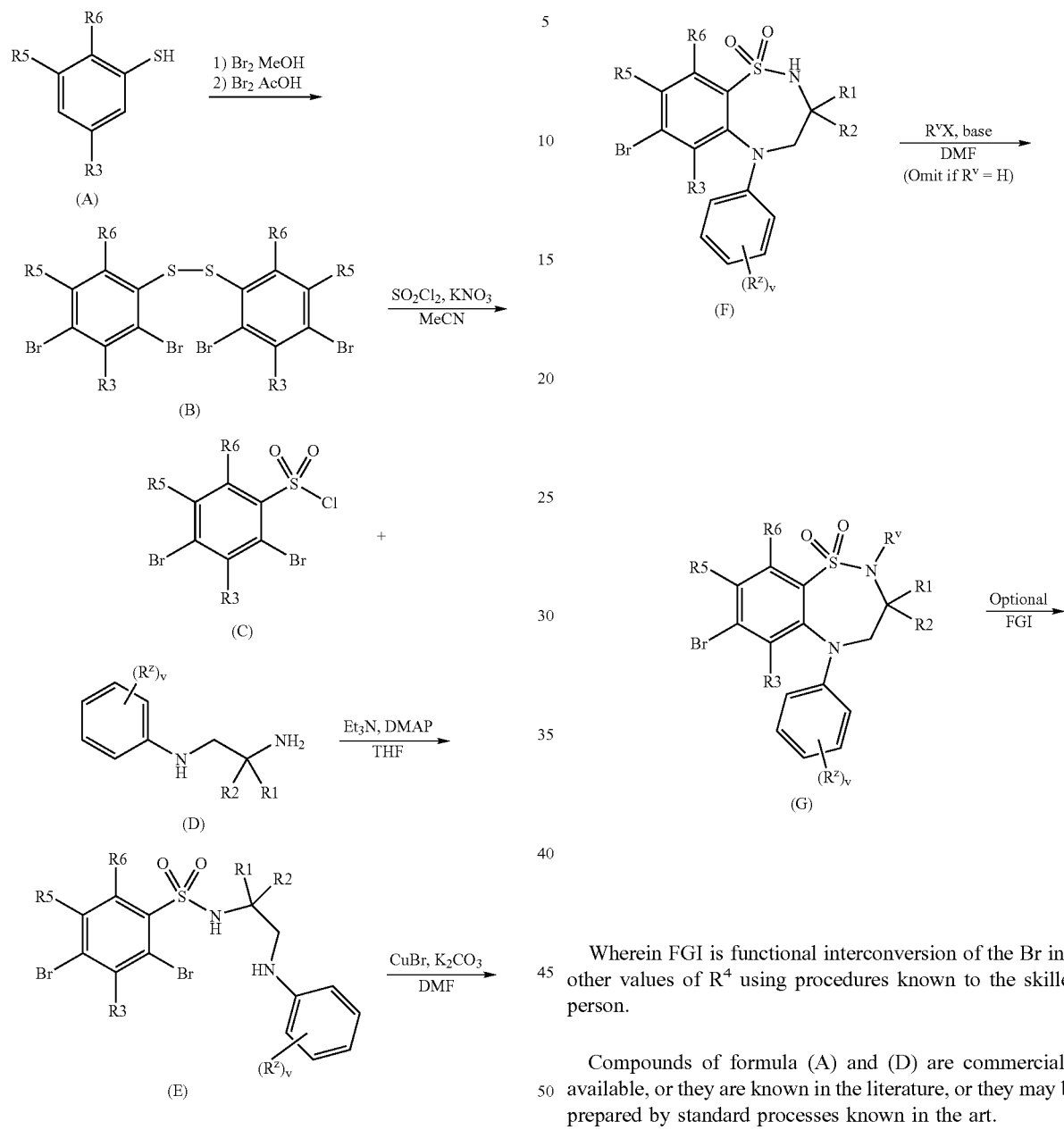
Wherein FGI is functional interconversion of the Br into other values of $R^4$ using procedures known to the skilled person.
Compounds of formula (A) and (D) are commercially available, or they are known in the literature, or they may be prepared by standard processes known in the art.
Scheme 1b
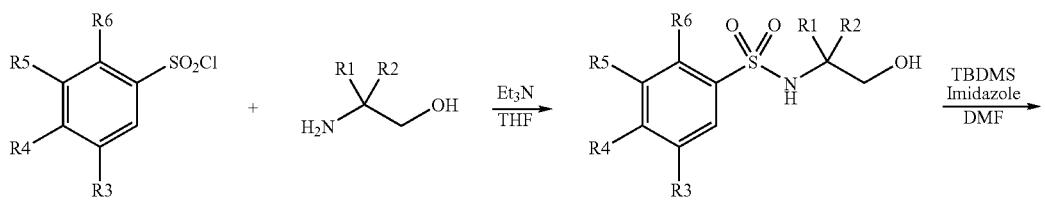

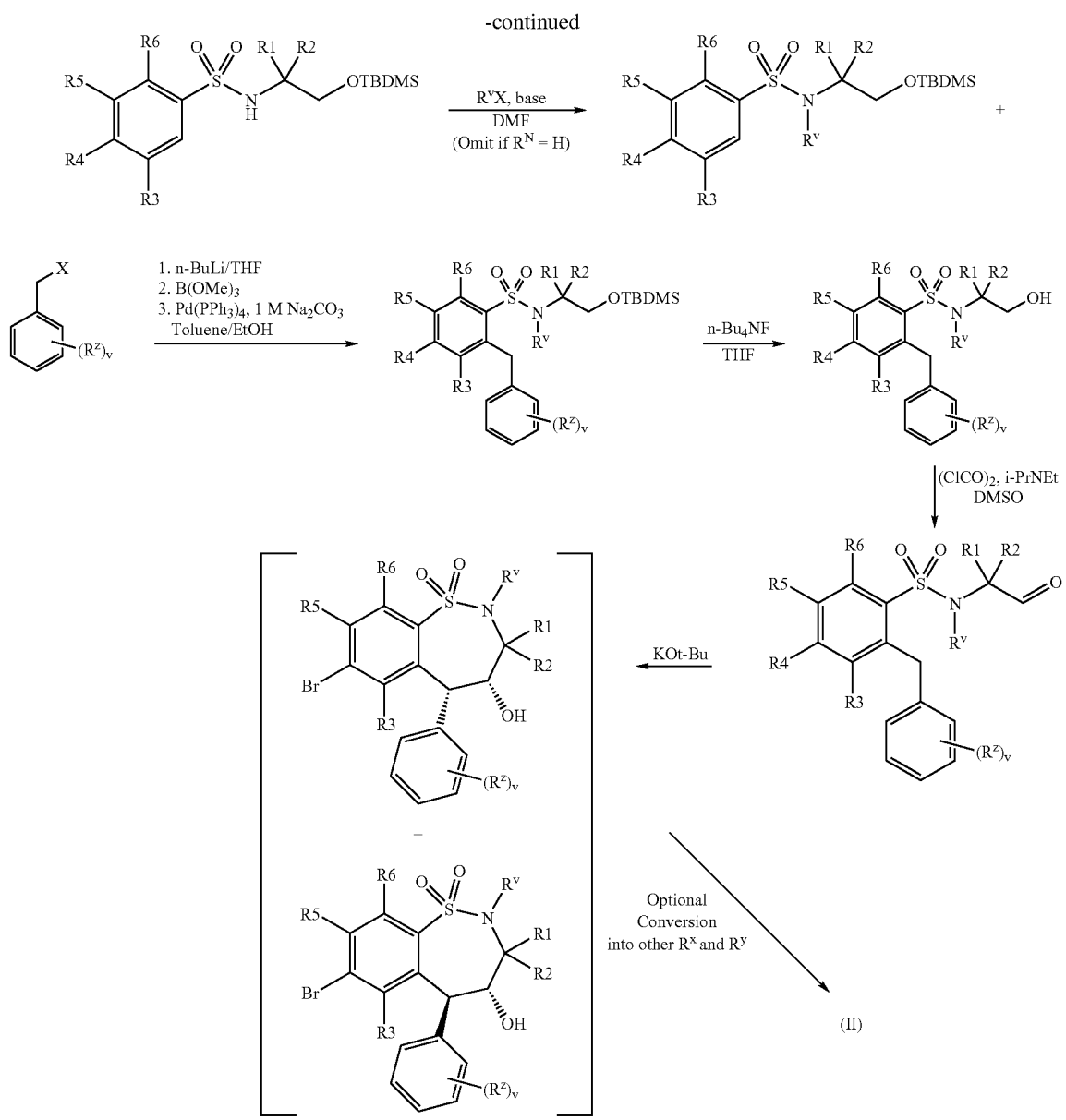

Process 1): Compounds of formula (IIa) or (IIb) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (III) are commercially available compounds, or they are known in the literature, or they are prepared by standard processes known in the art.

Process 2) and Process 3) and Process 7): Acids and amines may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (IVa) or (IVb) wherein X=—O—,—NR$^a$,—S— may be prepared according to Scheme 2:

Scheme 2

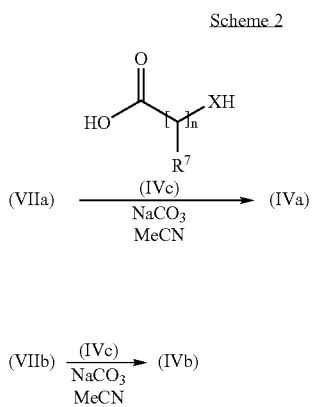

Wherein L in (VIIa) and (VIIb) is a displaceable group e.g. bromo, chloro, fluoro, mesyl or tosyl and wherein X is —O—, —S—, $NR^a$ (optionally for —SO— and —$SO_2$— followed by the oxidation step of Process 1).

Compounds of formula (IVa) and (IVb) where X is —SO— or —$SO_2$— may be prepared by oxidising the resulting compounds of formula (IVa) and (IVb) from Scheme 2 where X is —S—.

Compounds of formula (Va) or (Vb) wherein X is —$CH_2$— and n is 1 may be prepared according to Scheme 3.

The skilled person will appreciate that the above reaction scheme may be manipulated to prepare compounds of formula (Va) or (Vb) where n is 2 or 3.

Compounds of formula (XIa) and (XIb) may be prepared by manipulations known to the skilled person of the processes described herein.

Compounds of formula (IVc), (V), (VI), (XII) and (VII) are commercially available compounds, or they are known in the literature, or they are prepared by standard processes known in the art.

Process 4): Compounds of formula (VIIa) and (VIIb) maybe reacted with thiols of formula (VIII) in the presence of base, for example an inorganic base such as sodium carbonate or an organic base such as Hunigs base, in the presence of a suitable solvent such as DMF or THF at a temperature in the range of 0° C. to reflux.

Compounds of formula (VIIa) and (VIIb) may be prepared by any of the procedures above for the preparation of compounds of formula (I), but wherein one of $R^4$ and $R^5$ is L.

Compounds of formula (VII) are commercially available compounds, or they are known in the literature, or they are prepared by standard processes known in the art.

Process 5) and Process 6): Esters of formula (IXa), (IXb), (Xa) and (Xb) may be deprotected under standard conditions such as those described below, for Example they may be deprotected with sodium hydroxide in methanol at room temperature.

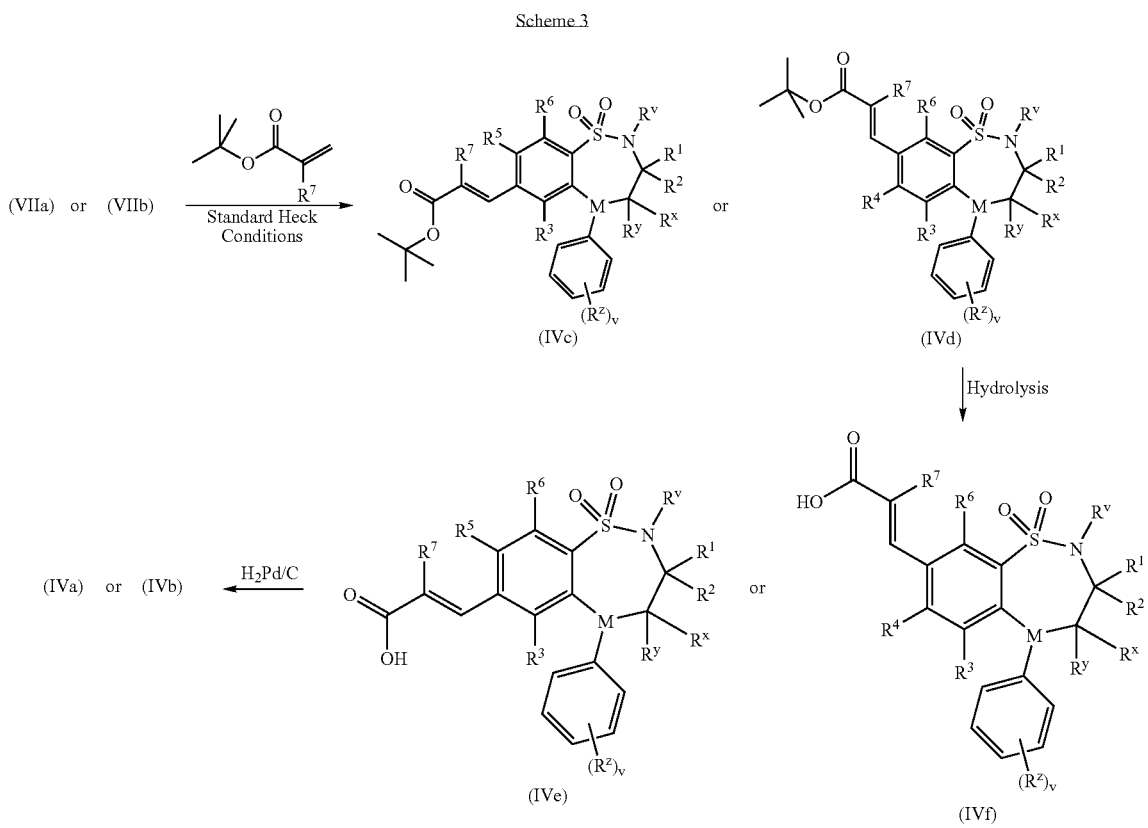

Esters of formula (IXa), (IXb), (Xa) and (Xb) may be prepared by any of the procedures above for the preparation of compounds of formula (I), but wherein $R^{11}$ or $R^{15}$ is $C_{1-4}$alkoxycarbonyl.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. A particular instance where a protecting group may be used is in protecting the nitrogen in the 2-position of the benzothiadiazepine ring during the synthesis of certain intermediates.

Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it maybe desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which maybe removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoy, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifing group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBAT-transfected cells (Smith L., Price-Jones M. J., Hugnes K. T. and Jones N. R. A.; J Biomolecular Screening, 3, 227–230) or in vivo by studying the effect on radiolabelled bile acid absorption in mice/rats (Lewis M. C., Brieaddy L. E. and Root C., J., J Lip Res 1995, 36, 1098–1105).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5–5000 mg per square meter body area of the animal, i.e. approximately 0.02–100 mg/kg, preferably 0.02–50 mg/kg, and this normally provides a therapeutically-effective dose. A unit dose form such as a tablet or capsule will usually contain, for example 1–250 mg of active ingredient. Preferably a daily dose in the range of 1–50 mg/kg, particularly 0.1–10 mg/kg is employed. In another aspect a daily dose in the rage of 0.02–20 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of atherosclerosis, coronary heart diseases, myocardial infarction, angina pectoris, peripheral vascular diseases, stroke and transient ischaemic attacks in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating atherosclerosis, coronary heart diseases, myocardial infarction, angina pectoris, peripheral vascular diseases, stroke and transient ischaemic attacks in a warm-blooded animal, such as man, in need of such treatment which comprises administering to said animal an effective amount of a compound of formula (I), or a pharmaceutically acceptable salt, solvate, solvate of such a salt or a prodrug thereof.

There is evidence that an IBAT inhibitor might potentially be useful in the treatment and/or prevention of gallstones. According to a further feature of this aspect of the invention there is provided a method of treating and/or preventing gallstones in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 0.1–50 mg/kg preferably 0.1–10 mg/kg is envisaged.

The IBAT inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl(methylsulphonyl)amino]pyrimidin-5-yl](3R, 5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a pro drug thereof. A preferable particular statin is rosuvastatin calcium salt.

In an additional aspect of the invention, the compound of formula (I), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof and a bile acid binder.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) a bile acid binder; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form;
c) a bile acid binder; in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) a bile acid binder; in a third unit dosage form; and
d) container means for containing said first, second and third dosage forms.

According to another feature of the invention there is provided the use of a compound of the formula (I), or a pharmaceutically acceptable salt, solvate, solvate of such a salt or a prodrag thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof; and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a farther aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded aninal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

- a CETP (cholesteryl ester transfer protein) inhibitor, for example those referenced and described in WO 00/38725 page 7 line 22-page 10, line 17 which are incorporated herein by reference;
- a cholesterol absorption antagonist for example azetidinones such as SCH 58235 and those described in U.S. Pat. No. 5,767,115 which are incorporated herein by reference;
- a MTP (microsomal transfer protein) inibitor for example those described in Science, 282, 751–54, 1998 which are incorporated herein by reference;
- a fibric acid derivative; for example clofibrate, gemfibrozil, fenofibrate, ciprofibrate and bezafibrate;
- a nicotinic acid derivative, for example, nicotinic acid (niacin), acipimox and niceritrol;
- a phytosterol compound for example stanols;
- probucol;
- an anti-obesity compound for example orlistat (EP 129,748) and sibutramine (GB 2,184,122 and U.S. Pat. No. 4,929,629);
- an antihypertensive compound for example an angiotensin converting enzyme inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, a diuretic or a vasodilator;
- insulin;
- sulphonylureas including glibenclamide, tolbutamide;
- metformin; and/or
- acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula (I) include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623–634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof. Additional suitable PPAR alpha and/or gamma agonists are NN622/Ragaglitazar and BMS 298585.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof; in a first unit dosage form;
b) a PPAR alpha and/or gamma agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, a PPAR alpha and/or gamma agonist, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention. For example compounds of formula (IXa), (IXb), (Xa) and (Xb) show IBAT inhibitory activity when tested in the above referenced in vitro test assay and are thus claimed as a further feature of the invention.

Thus in a further feature of the invention, there is provided a compound of formula (IXa), (IXb), (Xa) or (Xb), or a pharmaceutically acceptable salt, solvate, solvate of such a salt or a prodrug thereof.

Therefore according to a further aspect of the invention there is provided a pharmaceutical composition which comprises a compound of formula (IXa), (IXb), (Xa) or (Xb), or a pharmaceutically acceptable salt, solvate, solvate of such a salt or a prodrug thereof, as defined hereinbefore in association with a pharmaceutically-acceptable diluent or carrier.

According to an additional aspect of the present invention there is provided a compound of the formula (IXa), (IXb), (Xa) or (Xb), or a pharmaceutically acceptable salt, solvate, solvate of such a salt or a prodrug thereof, as defined hereinbefore for use in a method of prophylactic or therapeutic treatment of a warm-blooded animal, such as man.

Thus according to this aspect of the invention there is provided a compound of the formula (IXa), (IXb), (Xa) and (Xb), or a pharmaceutically acceptable salt, solvate, solvate of such a salt or a prodrug thereof, as defined hereinbefore for use as a medicament.

According to another feature of the invention there is provided the use of a compound of the formula (IXa), (IXb), (Xa) or (Xb), or a pharmaceutically acceptable salt, solvate, solvate of such a salt or a prodrug thereof as defined hereinbefore in the manufacture of a medicament for use in the production of an IBAT inhibitory effect in a warm-blooded animal, such as man.

According to another feature of the invention there is provided the use of a compound of the formula (IXa), (IXb), (Xa) or (Xb), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (IXa), (IXb), (Xa) or (Xb), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (IXa), (IXb), (Xa) or (Xb), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting examples, in which standard techniques known to the skilled chemist and techniques analogous to those described in these examples may be used where appropriate, and in which, unless otherwise stated:
(i) evaporations were carried out by rotary evaporation in vacuo and work up procedures were carried out after removal of residual solids such as drying agents by filtration;
(ii) all reactions were carried out under an inert atmosphere at ambient temperature, typically in the range 18–25° C., with solvents of HPLC grade under anhydrous conditions, unless otherwise stated;
(iii) column chromatography (by the flash procedure) was performed on Silica gel 40–63 μm (Merck);
(iv) yields are given for illustration only and are not necessarily the maximum attainable;
(v) the structures of the end products of the formula (I) were generally confirmed by nuclear (generally proton) magnetic resonance (NMR) and mass spectral techniques; magnetic resonance chemical shift values were measured in deuterated $CD_3OD$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer; and peak multiplicities are shown as follows: s, singlet; d, doublet; dd, double doublet; t, triplet; tt, triple triplet; q, quartet; tq, triple quartet; m, multiplet; br, broad; LCMS were recorded on a Waters ZMD, LC column xTerra MS $C_8$(Waters), detection with a HP 1100 MS-detector diode array equipped; mass spectra (MS) (loop) were recorded on VG Platform II (Fisons Instruments) with a HP-1100 MS-detector diode array equipped; unless otherwise stated the mass ion quoted is ($MH^+$);
(vi) unless further details are specified in the text, analytical high performance liquid chromatography (HPLC) was performed on Prep LC 2000 (Waters), Kromasil $C_8$, 7 μm, (Akzo Nobel); MeCN and de-ionised water 100 mM ammonium acetate as mobile phases, with suitable composition;
(vii) intermediates were not generally fully characterised and purity was assessed by thin layer chromatography (TLC), HPLC, infra-red (IR), MS or NMR analysis;
(viii) where solutions were dried sodium sulphate was the drying agent;
(ix) where an "ISOLUTE" column is referred to, this means a column containing 2 g of silica, the silica being contained in a 6 ml disposable syringe and supported by a porous disc of 54 Å pore size, obtained from International Sorbent Technology under the name "ISOLUTE"; "ISOLUTE" is a registered trade mark;
(x) the following abbreviations may be used hereinbefore or hereinafter:

| DCM | dichloromethane; |
|---|---|
| DMF | N,N-dimethylformamide; |
| TFA | trifluoroacetic acid; |
| TBTU | o-Benzotriazol-1-yl-N,N,N',N'-tetramethyluronium tetrafluoroborate; |
| EtOAc | ethyl acetate; and |
| MeCN | acetonitrile. |

Example 1

1,1-Dioxo-3,3-dibutyl-5-phenyl-7-bromo-8-(N-{(R)-α-[N-(carboxymethyl)carbamoyl] benzyl}carbamoylmethoxy)-2,3,4,5-tetrahydro-1,2, 5-benzothiadiazepine To a solution of 1,1-dioxo-3,3-dibutyl-5-phenyl-7-bromo-8-carboxymethoxy-2,3,4,5-tetrahydro-1,2,5-benzothiadiazepine (Method 2; 0.020 g, $3.71*10^{-5}$ mol) in DCM (4 ml) was added (R)-α-[N-(t-butoxycarbonylmethyl)carbamoyl] benzylamine (Method 5; 0.013 g, $4.82*10^{-5}$ mol) and N-methylmorpholine (0.015 ml, $1.48*10^{-4}$ mol). The mixture was stirred for 5 min and then TBTU (0.015 g, $4.82*10^{-5}$ mol) was added. The reaction mixture was stirred overnight and then TFA (1.5 ml) was added. After 1 hour, the solution was diluted with toluene, before the solvent was removed under reduced pressure. The residue was purified by preparative HPLC using an MeCN/ammonium acetate buffer as eluent. and freeze-dried, to give the title compound in 0.026 g (96%) as a white solid. NMR (400 MHz, DMSO-d6) 0.60–0.80 (m, 6H), 0.80–1.60 (m, 12H), 3.30 (dd (AB), 1H), 3.45 (dd (AB), 1H), 3.85 (brs, 2H), 4.70 (d (AB), 1H), 4.75 (d (AB), 1H), 5.60 (d, 1H), 6.90–7.50 (m, 12H), 8.00–8.10 (m,1H). 8.55 (d, 1H).

Example 2

1,1-Dioxo-3,3-dibutyl-5-phenyl-7-methylthio-8-(N-{(R)-α-[N-(carboxymethyl)carbamoyl]benzyl}carbamoylmethoxy)-2,3,4,5-tetrahydro-1,2,5-benzothiadiazepine To a solution of 1,1-dioxo-3,3-dibutyl-5-phenyl-7-methylthio-8-carboxymethoxy-2,3,4,5-tetrahydro-1,2,5-benzothiadiazepine (Method 3; 0.016 g, $3.16*10^{-5}$ mol) in DCM (4 ml) was added (R)-α-[N-(t-butoxycarbonylmethyl)carbamoyl]benzylamine (Method 5; 0.012 g, $4.54*10^{-5}$ mol) and N-methylmorpholine (0.015 ml, $1.48*10^{-4}$ mol). The mixture was stirred for 5 min and then TBTU (0.015 g, $4.82*10^{-5}$ mol) was added. The reaction mixture was stirred overnight and then TFA (1.5 ml) was added. After 1 hour, the solution was diluted with toluene, before the solvent was removed under reduced pressure. The residue was purified by preparative HPLC using an MeCN/ammonium acetate buffer as eluent and freeze-dried, to give the title compound in 0.018 g (82%) as a white solid. NMR (400 MHz, DMSO-d6) 0.65–0.80 (m, 6H), 0.85–1.60 (m, 12H), 2.10 (s, 3H), 3.65 (dd (AB), 1H), 3.75 (dd (AB), 1H), 3.85 (brs, 2H), 4.65 (d (AB), 1H), 4.75 (d (AB), 1H), 5.60 (d, 1H), 6.55 (s, 1H), 6.90–7.50 (m, 11H), 8.45 (d, 1H), 8.50–8.60 (m, 1H).

Example 3

1,1-Dioxo-3,3-dibutyl-5-phenyl-7-bromo-8-(N-{(R)-α-[N-(2-sulphoethyl)carbamoyl]-4-hydroxybenzyl}carbamoylmethoxy)-2,3,4,5-tetrahydro-1,2,5-benzothiadiazepine To a solution of 1,1-dioxo-3,3-dibutyl-5-phenyl-7-bromo-8-carboxymethoxy-2,3,4,5-tetrahydro-1,2,5-benzothiadiazepine (Method 2; 0.050 g, $9.27*10^{-5}$ mol) in DMF (6 ml) was added 2-{[(2R)-2-amino-2-(4-hydroxyphenyl)ethanoyl]amino}ethanesulphonic acid (Method 6; 0.033 g, $1.20*10^{-4}$ mol) and N-methylmorpholine (0.041 ml, $3.72*10^{-4}$ mol). The mixture was stirred for 10 min and then TBTU (0.039 g, $1.21*10^{-4}$ mol) was added. The reaction mixture was stirred overnight and the solvent was removed under reduced pressure. The residue was purified by preparative HPLC using an MeCN/ammonium acetate buffer as eluent and freeze-dried, to give the title compound in 0.039 g (53%) as a white solid. NMR (400 MHz, DMSO-d6) 0.60–0.80 (m, 6H), 0.80–1.60 (m, 12H), 2.40–2.60 (m, 2H), 3.10`3.50 (m, 2H), 3.85 (brs, 2H), 4.70 (d (AB), 1H), 4.75 (d (AB), 1H), 5.25 (d, 1H), 6.70 (s, 1H), 6.75 (s, 1H), 6.85–7.80 (m, 10H), 8.15–8.25 (m, 1H). 8.45 (d, 1H), 9.40 (brs, 1H).

Example 4

1,1-Dioxo-3,3-dibutyl-5-phenyl-7-methylthio-8-(N-{(R)-α-[N-((S)-1-carboxy-2-hydroxyethyl)carbamoyl]benzyl}carbamoylmethoxy)-2,3,4,5-tetrahydro-1,2,5-benzothiadiazepine A solution of 1,1-dioxo-3,3-dibutyl-5-phenyl-7-methylthio-8-carboxymethoxy-2,3,4,5-tetrahydro-1,2,5-benzothiadiazepine (Method 3; 0.050 g, 0.099 mmol), t-butyl N-[(2R)-2-amino-2-phenylethanoyl]-o-(t-butyl)-L-serinate (Method 14; 0.042 g, 0.120 mmol) and N-methylmorpholine (0.033 ml, 0.299 mmol) in DCM (4 ml) was stirred at RT for 10 min, after which TBTU (0.041 g, 0.128 mmol)) was added. After 8 h, the conversion was completed; m/z: 839.7. TFA (2 ml) was added and the reaction mixture was stirred for 12 hours. The solution was transferred to a separating funnel and washed twice with water and then concentrated. The residue was purified by preparative HPLC using a gradient of 40–60% MeCN in 0.1M ammonium acetate buffer as eluent. The title compound was obtained in 0.045 g (63%) as a white solid. NMR (400 MHz, DMSO-d6): 0.60–0.80 (6H, m), 0.85–1.60 (12H, m), 2.10 (3H, s), 3.40–3.65 (2H, m), 3.85 (2H, brs), 4.10–4.20 (1H, m), 4.70 (1H, d(AB)), 4.75 (1H, d(AB)), 5.70 (1H, d), 6.60 (1H, s), 6.85–7.50 (12H, m), 8.50 (1H, d), 8.60 (1H, d); m/z: 839.7.

Example 5

1,1-Dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine A solution of 1,1-dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 0.055 g, 0.086 mmol), L-alanine, 1,1-dimethylethyl ester, hydrochloride (0.017 g, 0.098 mmol) and N-methylmorpholine (0.028 ml, 0.254 mmol) in DCM (5 ml) was stirred at RT for 10 min, after which TBTU (0.033 g, 0.103 mmol) was added. After 16 h the conversion was complete; m/z: 767.4. TFA (2.5 ml) was added and the reaction mixture was stirred for 2 hours. The solution was diluted with toluene and then concentrated. The residue was purified by preparative HPLC using a gradient of 40–60% MeCN in 0.1M ammonium acetate buffer as eluent. The title compound was obtained in 0.044 g (72%) as a white solid. NMR (400 MHz): 0.70–0.85 (6H, m), 0.90–1.70 (12H, m), 1.30 (3H, d), 2.10 (3H, s), 3.95 (2H, brs), 4.25–4.40 (1H, m), 4.60 (1H, d(AB)), 4.65 (1H, d(AB)), 5.60 (1H, s), 6.60 (1H, s), 6.95–7.50 (11H, m); m/z: 767.4.

Example 6

1,1-Dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine A solution of 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 0.055 g, 0.086 mmol), butanoic acid, 2-amino-, 1,1-dimethylethyl ester, hydrochloride, (2S)-(0.020 g, 0.102 mmol) and N-methylmorpholine (0.035 ml, 0.316 mmol) in DCM (5 ml) was stirred at RT for 10 min, after which TBTU (0.036 g, 0.112 mmol) was added. After 19 h additional butanoic acid, 2-amino-, 1,1-dimethylethyl ester, hydrochloride, (2S)-(0.020 g, 0.102 mmol), N-methylmorpholine (0.035 ml, 0.316 mmol) and TBTU (0.036 g, 0.112 mmol) were added. After 68 h, the conversion was completed; m/z: 781.5. TFA (2 ml) was added and the reaction mixture was stirred for 7 h and then additional TFA (2 ml) was added. After 18 h the reaction was completed. The solution was transferred to a separating funnel and washed twice with water and then concentrated. The residue was purified by preparative HPLC using a gradient of 40–60% MeCN in 0.1M ammonium acetate buffer as eluent. The title compound was obtained in 0.026 g (41%) as a white solid. NMR (400 MHz, DMSO-$d_6$): 0.65 (3H, t), 0.65–0.80 (6H, m), 0.85–1.75 (14H, m), 2.10 (3H, s), 3.80 (2H, brs), 3.95–4.10 (1H, m), 4.65 (1H, d(AB)), 4.75 (1H, d(AB)), 5.65 (1H, d), 6.55 (1H, s), 6.85–7.50 (12H, m), 8.50 (1H, d), 8.60 (1H, d); m/z 781.5.

Example 7

1,1-Dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine A solution of 1,1-dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 0.055 g, 0.086 mmol), S-methyl-L-cysteine tert-butyl ester (Pestic. Sci.; EN; 45; 4; 1995; 357–362; 0.020 g, 0.105 mmol) and N-methylmorpholine (0.035 ml, 0.317 mmol) in DCM (5 ml) was stirred at RT for 10 min, after which TBTU (0.036 g, 0.112 mmol) was added. After 19 h additional S-methyl-L-cysteine tert-butyl ester (0.020 g, 0.105 mmol), N-methylmorpholine (0.035 ml, 0.317 mmol) and TBTU (0.036 g, 0.112 mmol) were added. After 68 h the conversion was complete; m/z: 811.6 (M-1)⁻. TFA (1.5 ml) was added and the reaction mixture was stirred for 7 h and additional TFA (1.5 ml) was added. After 18 h the reaction was complete. The solution was transferred to a separating funnel and washed twice with water and then concentrated. The residue was purified by preparative HPLC using a gradient of 40–60% MeCN in 0.1M ammonium acetate buffer as eluent. The title compound was obtained in 0.042 g (65%) as a white solid. NMR (400 MHz, DMSO-$d_6$): 0.65–0.80 (6H, m), 0.85–1.60 (12H, m), 1.85 (3H, s), 2.10 (3H, s), 2.60–2.80 (2H, m), 3.80 (2H, brs), 4.20–4.35 (1H, m), 4.65 (1H, d(AB)), 4.75 (1H, d(AB)), 5.65 (1H, d), 6.55 (1H, s), 6.85–7.50 (12H, m), 8.45 (1H, d), 8.65 (1H, d).

Example 8

1,1-Dioxo-3,3-dibutyl-5-phenyl-7-methylthio-8-(N-{(R)-α-[N-((S)-1-carboxy-2-carbamoylethyl)carbamoyl]benzyl}carbamoylmethoxy)-2,3,4,5-tetrahydro-1,2,5-benzothiadiazepine N-Methylmorpholine (0.034 ml, 0.314 mmol), TBTU (0.033 g, 0.103 mmol) and L-asparagine, 1,1-dimethylethyl ester, monohydrochloride (0.021 g, 0.093 mmol) was successively added to a solution of 1,1-dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 0.050 g, 0.078 mmol) in DCM (5 ml). After 2 h there were still starting material left and additional N-methylmorpholine (0.035 ml, 0.314 mmol) and TBTU (0.033 g, 0.103 mmol) were added. After 12 h the conversion was complete; m/z: 810.5. The solution was diluted with water (~5 ml) and then extracted three times with ether. The combined organic phases was dried over magnesium sulphate and concentrated. The residue was dissolved in a mixture of DCM (5 ml) and TFA (2.5 ml) and the solution was stirred for 21 hours. The solution was transferred to a separating funnel and washed with water and then concentrated. The residue was purified by preparative HPLC using a gradient of 40–60% MeCN in 0.1M ammonium acetate buffer as eluent. The title compound was obtained in 0.022 g (37%) as a white solid. NMR (400 MHz, DMSO-$d_6$): 0.60–0.80 (6H, m), 0.80–1.60 (12H, m), 2.10 (3H, s), 2.25–2.70 (2H, m), 3.80 (2H, brs), 4.35–4.45 (1H, m), 4.65 (1H, d(AB)), 4.75 (1H, d(AB)), 5.60 (1H, d), 6.55 (1H, s), 6.70–7.60 (14H, m), 8.45 (1H, d), 8.55–8.70 (1H, m); m/z 810.5.

Example 9

1,1-Dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine ammonium salt The title compound was synthesized using the procedure of Example 3 starting from 1,1-dioxo-3,3-dibutyl-5-phenyl-7-methylthio-8-carboxymethoxy-2,3,4,5-tetrahydro-1,2,5-benzothiadiazepine (Method 3; 43 mg, 0.085 mmol). The solvent was evaporated after 3 hours and the crude product was purified by preparative HPLC (C8 column, 50×250 mm) using a gradient (40/60 to 60/40) of MeCN/0.1M ammonium acetate buffer as eluent. Lyophilization yielded 38 mg (57% yield) of the title compound. NMR (400 MHz): 0.8 (t, 6H), 1.0–1.2 (m, 6H), 1.25–1.4 (m, 2H), 1.4–1.5 (m, 2H), 1.55–1.7 (m, 2H), 2.1 (s, 3H), 2.8–3.0 (m, 2H), 3.55–3.7 (m, 2H), 3.95 (brs, 2H), 4.6 (ABq, 2H), 5.35 (s, 1H), 6.6 (s, 1H), 6.75 (d, 2H), 7.05 (t, 1H) 7.15–7.4 (m, 7H), 8.15 (t, 1H); m/z: 763.

Example 10

1,1-Dioxo-3,3-dibutyl-5-phenyl-7-methylthio-8-(N-{(R)-α-[N-(carboxymethyl)carbamoyl]-4-hydroxybenzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 50 mg, 0.076 mmol) was dissolved in DCM (4 ml). Glycine tert-butyl ester (12 mg, 0.091 mmol), 2,6-lutidine (20 μl, 0.15 mmol) and TBTU (30 mg, 0.091 mmol) were added successively. After 3 h DMF (2 ml) was added and a clear solution was obtained. Glycine tert-butyl ester (0.04 mmol), 2,6-lutidine (0.15 mmol) and TBTU (2×0.03 mmol) were added and the mixture was stirred for an additional 3 h. The reaction mixture was concentrated and then extracted between aqueous KHSO₄ (0.05M, pH=1) and EtOAc (2×20 ml). The organic phase was washed with brine, dried and concentrated to yield an oil containing the tert-butyl ester of the title compound. M/z: 769 and 786 (M+18 ($NH_4^+$)). DCM (4 ml) and TFA (1.5 ml) were added. The mixture was stirred for 2 hours and was then concentrated and purified by preparative HPLC on a C8 column (50×250 mm) using a gradient (20/80 to 50/50) of MeCN/0.01M ammonium acetate buffer as eluent. Lyophilization yielded the title compound in 52% (28 mg). NMR (400 MHz) 0.8 (t, 6H), 1.0–1.2 (m, 6H), 1.25–1.4 (m, 2H), 1.4–1.5 (m, 2H), 1.55–1.7 (m, 2H), 2.1 (s, 3H), 3.9 (ABq, 2H), 3.95 (brs, 2H), 4.6 (ABq, 2H), 5.45 (s, 1H), 6.6 (s, 1H), 6.75 (d, 2H), 7.05 (t, 1H) 7.15–7.4 (m, 7H); m/z: 730 (M+18 ($NH_4^+$).

Example 11

1,1-Dioxo-3,3-dibutyl-5-phenyl-7-methylthio-8-(N-{(R-)-α-[N-((S)-1-carboxyethyl)carbamoyl]-4-hydroxybenzyl}carbamoylmethoxy)-2,3,4,5-tetrahydro-1,2,5-benzothiadiazepine The title compound was synthesized by the procedure described in Example 10 starting from 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 50 mg, 0.076 mmol) and tert-butyl L-alarinate hydrochloride. The intermediate tert-butyl ester of the title compound was confirmed. M/z: 783 and 800 (M+18 (NH$_4^-$)). Hydrolysis and purification by preparative HPLC yielded the title compound in 20 mg (37% yield). NMR (400 MHz) 0.8 (t, 6H), 1.0–1.2 (m, 6H), 1.25–1.4 (m, 2H), 1.3 (d, 3H), 1.4–1.5 (m, 2H), 1.55–1.7 (m, 2H), 2.1 (s, 3H), 3.95 (brs, 2H), 4.35 (q, 1H), 4.6 (ABq, 2H), 5.45 (s, 1H), 6.6 (s, 1H), 6.75 (d, 2H), 7.05 (t, 1H) 7.15–7.4 (m, 7H1); m/z: 744.

Example 12

1,1-Dioxo-3,3-dibutyl-5-phenyl-7-methylthio-8-(N-{(R)-α-[N-((S)-1-carboxy-2-hydroxyethyl)carbamoyl]-4-hydroxbenzyl}carbamoylmethoxy)-2,3,4,5-tetrahydro-1,2,5-benzothiadiazepine The title compound was synthesized by the procedure described in Example 10 starting from 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 50 mg, 0.076 mmol) and tert-butyl o-(tert-butyl)-L-serinate hydrochloride. The intermediate ester was confirmed; m/z: 755. Hydrolysis and purification by preparative HPLC yielded the title compound in 19 mg (33% yield). M/z: 743 (M+1). NMR (400 MHz): 0.8 (t, 6H), 1.0–1.2 (m, 6H), 1.25–1.4 (m, 2H), 1.4–1.5 (m, 2H), 1.55–1.7 (m, 2H), 2.1 (s, 3H), 3.65–3.8 (m, 2H), 3.95 (brs, 2H), 4.33 (t, 1H), 4.6 (ABq, 2H), 5.5 (s, 1H), 6.6 (s, 1H), 6.75 (d, 2H), 7.05 (t, 1H) 7.15–7.4 (m, 7H).

Example 13

1,1-Dioxo-3,3-dibutyl-5-phenyl-7-methylthio-8-(N-{(R)-α-[N-(2-sulphoethyl)carbamoyl]benzyl}carbamoylmethoxy)-2,3,4,5-tetrahydro-1,2,5-benzothiadiazepine ammonium salt 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) was dissolved in 3 ml DCM. Tetrabutylammonium taurine (88 mg, 0.236 mmol) was added and the mixture was stirred for 30 min. TBTU (30 mg, 0.093 mmol) was added and the mixture was stirred overnight. The solution was concentrated and purified by preparative HPLC using a C8 column (50×250 mm). A gradient (20/80 to 60/40) of MeCN/0.1M ammonium acetate buffer was used as eluent. Lyophilization yielded 43 mg of a product mixture, which was further purified by flash chromatography (5 g) using a gradient of 3–20% MeOH in DCM as eluent. The fractions containing the title compound were collected and concentrated. MeOH and water were added and lyophilization yielded 17 mg (29% yield). NMR (400 MHz) 0.8 (t, 6H), 1.0–1.2 (m, 6H), 1.25–1.4 (m, 2H), 1.4–1.5 (m, 2H), 1.55–1.7 (m, 2H), 2.1 (s, 3H), 2.85–3.0 (m, 2H), 3.5–3.7 (m, 2H), 3.95 (brs, 2H), 4.6 (ABq 2H), 5.45 (s, 1H), 6.6 (s, 1H), 7.05 (t, 1H) 7.15–7.45 (m, 10H); m/z: 747.

Example 14

1,1-Dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) was dissolved in 1 ml DMF and 1 ml DCM. o-tert-Butyl-(L)-threonine tert-butyl ester (22 mg, 0.095 mmol) and N-methylmorpholine (17 μl, 0.154 mmol) were added and the mixture was stirred for 20 min. TBTU (30 mg, 0.093 mmol) was added and the solution was stirred for 2 hours and concentrated. DCM (20 ml) was added and the solution was washed with 10 ml brine, dried and concentrated to 3 ml. The intermediate ester was confirmed; m/z: 853. TFA (0.5 ml) was added and the solution was stirred overnight. Additionally 0.5 ml TFA was added and after 3 h the mixture was concentrated and purified by preparative HPLC on a C8 column (50×250 mm). A gradient (20/80 to 60/40) of MeCN/0.1M ammonium acetate buffer was used as eluent. Lyophilization gave the title compound in 61% yield (36 mg). NMR (400 MHz) 0.8 (t, 6H), 0.9 (d, 3H), 1.0–1.2 (m, 6H), 1.25–1.4 (m, 2H), 1.4–1.5 (m, 2H), 1.55–1.7 (m, 2H), 2.1 (s, 3H), 3.95 (brs, 2H), 4.15–4.25 (m, 1H), 4.35 (d, 1H), 4.6 (ABq, 2H), 5.65 (s, 1H), 6.6 (s, 1H), 7.05 (t, 1H), 7.1 (d, 2H), 7.15–7.4 (m, 6H), 7.5 (d, 2H); m/z: 7.41.

Example 15

1,1-Dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) was dissolved in 2 ml DMF. tert-Butyl (L)-valinate (20 mg, 0.095 mmol) and N-methylmorpholine (17 μl, 0.154 mmol) were added and the mixture was stirred for 20 min. TBTU (30 mg, 0.093 mmol) was added and the solution was stirred overnight. Additional N-methylmorpholine (8 μl, 0.078 mmol) and TBTU (3×5 mg, 0.047 mmol) were added and the mixture was stirred overnight and concentrated. The residue was purified by flash chromatography (2 g) using EtOAc:hexane (3:7) as eluent. The collected fraction was washed with 5% NaHCO$_3$ (10 ml), 0.1M KHSO$_4$ (15 ml) and brine before it was dried and concentrated. The intermediate tert-butyl ester of the title compound was confirmed; m/z: 812 (M+18 (NH$_4^+$)). DCM (4 ml) and TFA (1.5 ml) were added and the mixture was stirred overnight, concentrated and purified by preparative HPLC on a C8 column (50×25 mm). A gradient (20/80 to 60/40) of MeCN/0.1M ammonium acetate buffer was used as eluent. Lyophilization gave the title compound in 31% yield (18 mg). NMR (400 MHz) 0.65–0.85 (m, 12H), 0.95–1.2 (m, 6H), 1.25–1.4 (m, 2H), 1.4–1.5 (m, 2H), 1.55–1.7 (m, 2H), 2.02–2.2 (m, 1H), 2.1 (s, 3H), 3.95 (brs, 2H), 4.3 (d, 1H), 4.6 (ABq, 2H), 5.65 (s, 1H), 6.6 (s, 1H), 7.05 (t, 1H), 7.2 (d, 2H), 7.25–7.4 (m, 6H), 7.5 (d, 2H); m/z: 739.

Example 16

1,1-Dioxo-3,3-dibutyl-5-phenyl-7-methylthio-8-(N-{(R)-α-[N-((S)-1-carboxy-3-methylbutyl)carbamoyl]benzyl}carbamoylmethoxy)-2,3,4,5-tetrahydro-1,2,5-benzothiadiazepine The title compound was synthesized by the procedure given in Example 15 starting from 1,1-dioxo-3,3-dibutyl-5-phenyl-7-methylthio-8-[N-((R)-α-carboxybenzl)carbamoylmethoxy]-2,3,4,5-tetrahydro-1,2,5-benzothiadiazepine (Example 25; 50 mg, 0.078 mmol) and tert-butyl (L)-leucinate (21 mg, 0.095 mmol). The DMF was removed and 20 ml EtOAc was added and washed with NaHCO$_3$ (5%, 10 ml), 0.1M KHSO$_4$ (15 ml) and brine before it was dried and concentrated. The resulting residue was purified by flash chromatography as described. The intermediate tert-butyl ester of the title compound was confirmed; m/z: 826 (M+18 (NH$_4^+$)). Hydrolysis and purification by preparative HPLC gave the title compound in 21% yield (12 mg). NMR (400 MHz) 0.7 (dd, 6H), 0.75–0.85 (m, 6H), 0.95–1.2 (m, 6H), 1.25–1.7 (m, 9H), 2.1 (s, 3H), 3.95 (brs, 2H), 4.3–4.4 (m, 1H), 4.6 (ABq, 2H), 5.55 (s, 1H), 6.6 (s, 1H), 7.05 (t, 1H), 7.2 (d, 2H), 7.25–7.4 (m, 6H) 7.5 (d, 2H; m/z: 753.

Example 17

1,1-Dioxo-3,3-dibutyl-5-phenyl-7-methylthio-8-(N-{(R)-α-[N-(1-(S)-1-carboxy-2-(S)-2-methylbutyl)carbamoyl]benzyl}carbamoylmethoxy)-2,3,4,5-tetrahydro-1,2,5-benzothiadiazepine The title compound was synthesized by the procedure given in Example 15 starting from 1,1-dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) and tert-butyl (L)-isoleucinate (21 mg, 0.095 mmol). The DMF was removed and 20 ml EtOAc was added and washed with NaHCO$_3$ (5%, 10 ml), 0.1M KHSO$_4$ (15 ml) and brine before it was dried and evaporated. No purification by flash chromatography was performed. The intermediate tert-butyl ester of the title compound was confirmed; m/z: 809. Hydrolysis and purification by preparative HPLC gave the title compound in 37% yield (22 mg). NMR (400 MHz) 0.65–1.4 (m, 22H), 1.4–1.5 (m, 2H), 1.5–1.7 (m, 2H), 1.75–1.85 (m, 1H), 2.1 (s, 3H), 3.95 (brs, 2H), 4.25 (d, 1H), 4.6 (ABq, 2H), 5.6 (s, 1H), 6.6 (s, 1H), 7.05 (t, 1H), 7.2 (d, 2H), 7.25–7.4 (m, 6H), 7.45 (d, 2H); m/z: 753.

Example 18

1,1-Dioxo-3,3-dibutyl-5-phenyl-7-methylthio-8-[N-((R)-α-carboxy-4-hydroxybenzl)carbamoylmethoxy]-2,3,4,5-tetrahydro-1,2,5-benzothiadiazepine 1,1-Dioxo-3,3-dibutyl-5-phenyl-7-methylthio-8-carboxymethoxy-2,3,4,5-tetrahydro-1,2,5-benzothiadiazepine (Method 3; 295 mg, 0.58 mmol) was dissolved in 10 ml DCM. 4-(1-(R)-t-Butoxycarbonyl-1-aminomethyl)phenol (Method 7; 160 mg, 0.72 mmol), 2,6-lutidine (140 µl, 1.20 mmol) and TBTU (230 mg, 0.72 mmol) were added successively. The mixture was stirred for 3 h. Additionally 4-(1-(R)-t-butoxycarbonyl-1-aminomethyl)phenol (10 mg, 0.04 mmol) was added and stirring was continued for 2 h. DCM (20 ml) was added and the solution was washed with NaHCO$_3$ (5%, 20 ml), KHSO$_4$ (0.3M; 20 ml), brine (20 ml) before it was dried and concentrated to a volume of 10 ml. The tert-butyl ester of the title compound was confirmed; m/z: 729 (M+18 (NH$_4^+$)). TFA (1.3 ml) was added and the mixture was stirred for 4.5 h and concentrated. The crude product was purified by preparative HPLC using a C8 column (5×500 mm) and a gradient (40/60 to 70/30 over 40 min) of MeCN/0.1M ammonium acetate buffer as eluent. Lyophilization yielded the title compound in 77.5% (302 mg). NMR (400 MHz) 0.8 (t, 6H), 1.0–1.2 (m, 6H), 1.25–1.4 (m, 2H), 1.4–1.5 (m, 2H), 1.55–1.7 (m, 2H), 2.1 (s, 3H), 3.95 (brs, 2H), 4.6 (ABq, 2H), 5.3 (s, 1H), 6.6 (s, 1H), 6.75 (d, 2H), 7.05 (t, 1H) 7.15–7.4 (m, 7H); m/z: 673 (M+18 (NH$_4^+$)).

Example 19

1,1-Dioxo-3,3-dibutyl-5-phenyl-7-methylthio-8-(N-{(R)-α-[N-((S)-1-carboxy-4-aminobutyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-{N-[(S)-1-(t-butoxycarbonyl)-4-(benzyloxycarbonylamino)butyl]carbamoyl}benzyl)carbamoylmethoxy]-2,3,4,5-tetrahydro-1,2,5-benzothiadiazepine (Method 8; 0.006 mg) was dissolved in DCM (0.2 ml), TFA (1 ml) was added and the reaction mixture was stirred at room temperature for 1 hour. DCM and TFA were removed at reduced pressure and the residue was purified by preparative HPLC using MeCN/NH4$^+$ buffer 50/50 as eluent. The acetonitrile was evaporated and lyophilisation gave the title compound in 37% yield (21.9 mg). M/z: 754.4 and 752.4 (M–H)$^-$.

Example 20

1,1-Dioxo-3,3-dibutyl-5-phenyl-7-methylthio-8-[N-((R)-α-{N-[(S)-1-carboxy-4-(benzyloxycarbonylamino)butyl]carbamoyl}benzyl)carbamoylmethoxy]-2,3,4,5-tetrahydro-1,2,5-benzothiadiazepine 1,1-Dioxo-3,3-dibutyl-5-phenyl-7-methylthio-8-[N-((R)-α-{N-[(S)-1-(t-butoxycarbonyl)-4-(benzyloxycarbonylamino)butyl]carbamoyl}benzyl)carbamoylmethoxy]-2,3,4,5-tetrahydro-1,2,5-benzothiadiazepine (Method 8; 0.006 mg) was dissolved in DCM (0.1 ml), TFA (0.15 ml) was added and the reaction mixture was stirred at room temperature for 1 hour. DCM and TFA were removed at reduced pressure and the residue was purified by preparative HPLC using MeCN/NH4$^+$ buffer 55/45 as eluent. The acetonitrile was evaporated and lyophilisation gave the title compound in 35% yield (2 mg). M/z: 888.7 and 886.7 (M–H)$^-$.

Example 21

1,1-Dioxo-3,3-dibutyl-5-phenyl-7-methylthio-8-{N-[(R)-α-((S)-2-carboxypyrrolidin-1-ylcarbonyl)benzyl]carbamoylmethoxy}-2,3,4,5-tetrahydro-1,2,5-benzothiadiazepine 1,1-Dioxo-3,3-dibutyl-5-phenyl-7-methylthio-8-(N-{(R)-α-[(S)-2-(t-butoxycarbonyl)pyrrolidin-1-ylcarbonyl]benzyl}carbamoylmethoxy)-2,3,4,5-tetrahydro-1,2,5-benzothiadiazepine (Method 10; 41 mg, 0.052 mmol) was dissolved in DCM:TFA 4:1 (3 ml) and stirred for 3 hours. The reaction mixture was evaporated under reduced pressure. The residue was purified by preparative HPLC using an acetonitrile/ammonium acetate buffer gradient (5/95 to 100/0) as eluent. 26.5 mg (70%) of the title compound was obtained after lyophilisation. M/z 737.3034.

Example 22

1,1-Dioxo-3,3-dibutyl-5-phenyl-7-methylthio-8-(N-{(R)-α-[N-(carboxymethyl)-N-methylcarbamoyl]benzyl}carbamoylmethoxy)-2,3,4,5-tetrahydro-1,2,5-benzothiadiazepine The title compound was synthesized from 1,1-dioxo-3,3-dibutyl-5-phenyl-7-methylthio-8-(N-{R)-α-[N-(t-butoxycarbonylmethyl)-N-methylcarbamoyl]benzyl}carbamoylmethoxy)-2,3,4,5-tetrahydro-1,2,5-benzothiadiazepine (Method 11) by the method of Example 21. NMR (500 MHz, 2 rotamers 3:1 mixture): Major rotamer: 0.8 (brt, 6H), 1.0–1.24 (m, 6H), 1.25–1.4 (m, 2H), 1.4–1.51 (m, 2H), 1.56–1.68 (m, 2H), 2.09 (s, 3H), 3.0 (s, 3H) 3.75–4.21 (m, 4H), 4.60 (ABq, 2H), 6.01 (s, 1H), 6.58 (s, 1H), 7.05 (t, 1H), 7.16–7.28 (m, 3H), 7.3–7.45 (m, 5H), 7.48 (brd, 2H) additional peaks from the minor rotamer at 2.14 (s), 3.0 (s), 4.56 (Abq), 5.81 (s), 6.61 (brs); m/z 711.4.

Example 23

1,1-Dioxo-3,3-dibutyl-5-phenyl-7-methylthio-8-(N-{(R)-α-[N-(1-(R)-2-(R)-1-carboxy-1-hydroxyprop-2-yl)carbamoyl]benzyl}carbamoylmethoxy)-2,3,4,5-tetrahydro-1,2,5-benzothiadiazepine The title compound was synthesized from 1,1-dioxo-3,3-dibutyl-5-phenyl-7-methylthio-8-[N-((R)-α-{N-[1-(R)-2-(R)-1-(t-butoxycarbonyl)-1-hydroxy-prop-2-yl]carbamoyl}benzyl)carbamoylmethoxy]-2,3,4,5-tetrahydro-1,2,5-benzothiadiazepine (Method 12) by the method of Example 21. M/z 741.3.

Example 24

1,1-Dioxo-3,3-dibutyl-5-phenyl-7-methylthio-8-(N-{(R)-α-[N-(sulphomethyl)carbamoyl]benzyl}carbamoylmethoxy)-2,3,4,5-tetrahydro-1,2,5-benzothiadiazepine ammonium salt 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol), aminomethanesulfonic acid (15 mg, 0.088 mmol) and N-methylmorpholine (17.2 µl, 0.156 mmol) were dissolved in DMF (2 ml). Tetrabutylammoniumhydrogensulfate (35 mg, 0.103 mmol) was added and the mixture was heated for 15 minutes at 60° C. After removing heating TBTU (45 mg, 0.14 mmol) was added. The reaction mixture was stirred in room temperature 40 minutes then 60° C. for one hour. After being stirred overnight 35 mg TBTU was added. After 6 hours 29 mg TBTU in small portions was added and the reaction mixture was stirred overnight. The mixture was evaporated under reduced pressure. The product was purified using preparative HPLC using an acetonitrile/ammonium acetate buffer gradient (5/95 to 100/0) as eluent. To give 10 mg (17%) of the title compound as a ammonium salt. NMR (600 MHz) 0.77 (brt, 6H), 0.97–1.22 (m, 6H), 1.24–1.48 (m, 4H), 1.51–1.68 (m 2H), 2.08 (s, 3H), 3.7–4.18 (m, 2H), 4.24 (d, 1H), 4.39 (d, 1H), 4.62 (ABq, 2H), 5.62 (s, 1H), 6.58 (brs, 1H), 7.02 (brt, 1H), 7.14–7.23 (m, 2H), 7.24–7.36 (m, 6H), 7.45 (d, 2H),; m/z 732.9.

Example 25

1,1-Dioxo-3,3-dibutyl-5-phenyl-7-methylthio-8-[N-((R)-α-carboxybenzyl)carbamoylmethoxyl]-2,3,4,5-tetrahydro-1,2,5-benzothiadiazepine 1,1-Dioxo-3,3-dibutyl-5-phenyl-7-methylthio-8-{N-[(R)-α-(t-butoxycarbonyl)benzyl]carbamoylmethoxy}-2,3,4,5-tetrahydro-1,2,5-benzothiadiazepine (Method 9; 762 mg, 1.09 mmol) was dissolved in a mixture of TFA (6.65 ml) and triethylsilane (0.350 ml). The reaction mixture was stirred for one hour and then evaporated under reduced pressure to give the title compound in a quantitative yield (714 mg). NMR (500 MHz): 0.8 (brt, 6H), 0.96–1.25 (m, 6H), 1.25–1.4 (m, 2H), 1.42–1.51 (m, 2H), 1.57–1.69 (m, 2H), 2.11 (s, 3H), 3.8–4.15 (m, 2H), 4.66 (ABq, 2H), 5.49–5.53 (m, 1H), 6.61 (s, 1H), 7.06 (t, 1H), 7.18–7.26 (m, 2H), 7.28–7.45 (m, 8H), 8.35 (d, NH); m/z 640.2.

Example 26

1,1-Dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 100 mg, 0.152 mmol) was dissolved in 3 ml DMF. o-tert-Butyl-(L)-threonine tert-butyl ester (50 mg, 0.216 mmol) and N-methylmorpholine (34 µl, 0.309 mmol) were added and the mixture was stirred for 5 min. TBTU (60 mg, 0.187 mmol) was added and the solution was stirred for 30 min. Formic acid (1–2 drops) was added and the mixture was extracted between EtOAc and water. The aqueous phase was washed with EtOAc and the combined organic phases were washed with 2% NaHCO₃, brine, dried and concentrated. The intermediate t-butyl ester of the title compound was confirmed; m/z: 869. DCM (3 ml) and TFA (0.5 ml) were added and the solution was stirred overnight. The mixture was concentrated and purified by preparative HPLC on a C8 column (50×250 mm). A gradient (20/80 to 50/50) of MeCN/0.1M ammonium acetate buffer was used as eluent. Lyophilization gave the title compound in 61% yield (71 mg). NMR (400 MHZ) 0.78 (t, 6H), 0.93 (d, 3H), 1.0–1.22 (m, 6H), 1.25–1.14 (m, 2H), 1.4–1.52 (m, 2H), 1.55–1.7 (m, 2H), 2.1 (s, 3H), 3.95 (brs, 2H), 4.18–4.25 (m, 1H), 4.35 (d, 1H), 4.63 (ABq, 2H), 5.53 (s, 1H), 6.57 (s, 1H), 6.75 (d, 2H), 7.03 (t, 1H), 7.2 (d, 2H), 7.23–7.37 (m, 5H); m/z: 757.

Example 27

1,1-Dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine The title compound was synthesized by the procedure described in Example 26 starting from 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 70 mg, 0.108 mmol) and tert-butyl (L)-valinate (31 mg, 0.148 mmol). The intermediate tert-butyl ester of the title compound was confirmed. M/z: 811. Hydrolysis and purification by preparative HPLC yielded the title compound in 56 mg (69% yield). NMR (400

MHz) 0.7–0.75 (m, 16H), 0.79 (t, 6H), 0.96–1.24 (m, 6H), 1.25–1.4 (m, 2H), 1.4–1.5 (m, 2H), 1.54–1.7 (m, 2H), 2.0–2.2 (m, 1H), 2.1 (s, 3H), 3.95 (brs, 2H), 4.22 (d, 1H), 4.6 (ABq, 2H), 5.54 (s, 1H), 6.58 (s, 1H), 6.75 (d, 2H), 7.03 (t, 1H), 7.2 (d, 2H), 7.23–7.37 (m, 5H); m/z: 7.55.

Example 28

1,1-Dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-trahydro-1,2,5-benzothiadiazepine The title compound was synthesized by the procedure described in Example 26 starting from 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 36 mg, 0.054 mmol) and tert-butyl (L)-norvalinate hydrochloride (16 mg, 0.076 mmol). The intermediate tert-butyl ester of the title compound was confirmed. M/z: 811. Hydrolysis and purification by preparative HPLC yielded the title compound in 23 mg (56% yield). NMR (400 MHz) 0.7–0.85 (m, 9H), 0.97–1.22 (m, 8H), 1.25–1.4 (m, 2H), 1.4–1.5 (m, 2H), 1.5–1.8 (m, 4H), 2.1 (s, 3H), 3.95 (brs, 2H), 4.27 (dd, 1H), 4.6 (ABq, 2H), 5.45 (s, 1H), 6.58 (s, 1H), 6.75 (d, 2H), 7.03 (t, 1H), 7.19 (d, 2H), 7.23–7.37 (m, 5H); m/z: 755.

Example 29

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2 5-benzothiadiazepine A solution of 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 0.075 g, 0.114 mmol), butanoic acid, 2-amino-, 1,1-dimethylethyl ester, hydrochloride, (2S)-(0.031 g, 0.160 mmol) and N-methylmorpholine (0.050 ml, 0.457 mmol) in DMF (4 ml) was stirred at RT for 10 min, after which TBTU (0.048 g, 0.149 mmol) was added. After 1 h, the conversion to the ester was complete. M/z: 797.4. The solution was diluted with toluene and then concentrated. The residue was dissolved in a mixture of DCM (5 ml) and TFA (2 ml) and the mixture was stirred for 7 h. The solvent was removed under reduced pressure. The residue was purified by preparative HPLC using a gradient of 20–60% MeCN in 0.1M ammonium acetate buffer as eluent. The title compound was obtained in 0.056 g (66%) as a white solid. NMR (400 MHz, DMSO-$d_6$): 0.70 (3H, t), 0.70–0.80 (6H, m), 0.85–1.75 (14H, m), 2.10 (3H, s), 3.80 (2H, brs), 4.00–4.15 (1H, m), 4.65 (1H, d(AB)), 4.70 (1H, d(AB)), 5.50 (1H, d), 6.60 (1H, s), 6.65–7.40 (11H, m), 8.35 (1H, d), 8.50 (1H, d) 9.40 (1H, brs).

Example 30

1,1-Dioxo-3,3-5-phenyl-7-methylthio-8-(N-{(R)-α-[N-((R)-1-carboxy-2-methylthioethyl)carbamoyl]-4-hydroxybenzyl}carbamoylmethoxy)-2,3,4,5-tetrahydro-1,2,5-benzothiadiazepine A solution of 1,1-dioxo-3,3-dibutyl-5-phenyl-7-methylthio-8-[N-((R)-α-carboxy-4-hydroxybenzyl) carbamoylmethoxy]-2,3,4,5-tetrahydro-1,2,5-benzothiadiazepine (Example 18, 0.075 g, 0.114 mmol), S-methyl-L-cysteine tert-butyl ester (Pestic. Sci.; EN; 45; 4; 1995; 357–362; 0.031 g, 0.160 mmol) and N-methylmorpholine (0.050 ml, 0.457 mmol) in DMF (4 ml) was stirred at RT for 10 min, after which TBTU (0.048 g, 0.149 mmol) was added. After 1 h, the conversion to the ester was complete. M/z: 829.5. The reaction mixture was diluted with formic acid (15 ml) and stirred at 50° C. for 17 h. The solution was diluted with toluene and then concentrated. The residue was purified by preparative HPLC using a gradient of 20–60% MeCN in 0.1M ammonium acetate buffer as eluent. The title compound was obtained in 0.070 g (79%) as a white solid. NMR (400 MHz, DMSO-$d_6$): 0.605–0.80 (6H, m), 0.80–1.60 (12H, m), 1.85 (3H, s), 2.10 (3H, s), 2.60–2.80 (2H, m), 3.85 (2H, brs), 4.15–4.3 (1H, m), 4.65 (1H, d(AB)), 4.70 (1H, d(AB)), 5.50 (1H, d), 6.60 (1H, s), 6.60–7.35 (11H, m), 8.30 (1H, d), 8.40 (1H, d), 9.40 (1H, brs).

Example 31

1,1-Dioxo-3,3-dibutyl-5-phenyl-7-methyl-8-(N-{(R)-α-[N-(carboxymethyl)carbamoyl]benzyl}carbamoylmethoxy)-2,3,4,5-tetrahydro-1,2,5-benzothiadiazepine A solution of 1,1-dioxo-3,3-dibutyl-5-phenyl-7-methyl-8-carboxymethoxy-2,3,4,5-tetrahydro-1,2,5-benzothiadiazepine (Method 5; 0.050 g, 0.105 mmol), (R)-α-[N-(t-butoxycarbonylmethyl)carbamoyl]benzylamine (Method 86 of WO 02/50051; 0.039 g, 0.148 mmol) and N-methylmorpholine (0.046 ml, 0.417 mmol) in DCM (4 ml) was stirred at RT for 20 min, after which TBTU (0.044 g, 0.137 mmol) was added. After 1 h, the conversion to the ester (m/z: 721.2 (M+1)$^+$) was completed. The solvent was removed under reduced pressure and the residue was dissolved in formic acid (5 ml). The solution was stirred for 17 hours and then concentrated. The residue was purified by preparative HPLC using a gradient of 40–60% MeCN in 0.1M ammonium acetate buffer as eluent. The title compound was obtained in 0.044 g (63%) as a white solid. NMR (400 MHz, DMSO-$d_6$): 0.65–0.80 (6H, m), 0.85–1.60 (12H, m), 2.10 (3H, s), 3.40–3.65 (2H, m), 3.70 (2H, bs), 4.60 (1H, d(AB)), 4.70 (1H, d(AB)), 5.55 (1H, d), 6.70 (1H, s), 6.80–7.50 (12H, m), 8.20–8.30 (1H, m), 8.55 (1H, d).

Example 32

1,1-Dioxo-3,3-dibutyl-5-phenyl-7-methyl-8-(N-{(R)-α-[N-((S)-1-carboxyropyl)carbamoyl]-4-hydroxybenzyl}carbamoylmethoxy)-2,3,4,5-tetrahydro-1,2,5-benzothiadiazepine A solution of 1,1-dioxo-3,3-dibutyl-5-phenyl-7-methyl-8-carboxymethoxy-2,3,4,5-tetrahydro-1,2,5-benzothiadiazepine (Method 16; 0.050 g, 0.105 mmol), (R)-α-{N-[(S)-1-(t-butoxycarbonyl)propyl]carbamoyl}-4-hydroxybenzylamine (Method 19; 0.045 g, 0.146 mmol) and N-methylmorpholine (0.047 ml, 0.427 mmol) in DCM (4 ml) was stirred at RT for 15 min, after which TBTU (0.044 g, 0.137 mmol) was added. After 17 h, the conversion to the ester (m/z: 765.7 (M+1)$^+$) was completed. The solvent was removed under reduced pressure and the residue was dissolved in formic acid (5 ml). The solution was stirred for 3 days and then concentrated. The residue was purified by preparative HPLC using a gradient of 40–60% MeCN in 0.1M ammonium acetate buffer as eluent. The title compound was obtained in 0.017 g (23%) as a white solid. NMR (400 MHz, DMSO) 0.60 (3H, t), 0.65–0.80 (6H, m), 0.85–1.75 (14H, m), 2.10 (3H, s), 3.75 (2H, bs), 3.90–4.05 (1H, m), 4.60 (1H, d(AB)), 4.65 (1H, d(AB)), 5.50 (1H, d), 6.65–7.30 (11H, m), 8.15 (1H, d), 8.40 (1H, d).

Example 33

1,1-Dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-(N-{(R)-α-[N-((S)-1-{N-[(S)-2-(t-butoxy)-1-(t-butoxycarbonyl)ethyl]carbamoyl}propyl)carbamoyl]benzyl}carbamoylmethoxy)-2,3,4,5-tetrahydro-1,2,5-benzothiadiazepine (Method 20; 14 mg, 0.015 mmol) was dissolved in a mixture of DCM:TFA (3:1, 4 ml). The reaction mixture was stirred for 3.5 hours. The solvent was evaporated under reduced pressure. The product was purified by preparative HPLC using a MeCN/0.1 M ammonium acetate buffer gradient (5/95 to 100/0) as eluent to give the title compound, 8 mg (65%). NMR (400 MHz): 0.7–0.83 (m, 9H), 0.9–1.40 (m, 8H), 1.40–1.52 (m, 2H), 1.52–1.70 (m, 3H), 1.77–1.88 (m, 1H), 2.11 (s, 3H), 3.84–4.1 (m, 4H), 4.29 (dd, 1H), 4.37 (t, 1H), 4.63 (ABq, 2H), 5.57 (s, 1H), 6.60 (s, 1H), 7.04 (brt, 1H), 7.20 (brd, 2H), 7.25–7.40 (m, 6H), 7.47 (d, 2H); m/z 812.3.

Example 34

1,1-Dioxo-3,3-dibutyl-5-phenyl-7-methylthio-8-(N-{(R)-α-[2-(S)-2-(carboxy)-4-(R)-4-(hydroxy)pyrrolidin-1-ylcarbonyl]benzyl}carbamoylmethoxy)-2,3,4,5-tetrahydro-1,2,5-benzothiadiazepine 1,1-Dioxo-3,3-dibutyl-5-phenyl-7-methylthio-8-(N-{(R)-α-[2-(S)-2-(methoxycarbonyl)-4-(R)-4-(hydroxy)pyrrolidin-1-ylcarbonyl]benzyl}carbamoylmethoxy)-2,3,4,5-tetrahydro-1,2,5-benzothiadiazepine (Method 21; 23 mg, 0.030 mmol) was dissolved in TBF:H$_2$O (1:1, 1 ml). Lithium hydroxide (monohydrate, 2 mg, 0.048 mmol) was added and the mixture was stirred for 2 hours. 50% Starting material remained so additional lithium hydroxide (3 mg) was added and left for an hour. The reaction was still not complete so further lithium hydroxide (2 mg) was added and the reaction was stirred overnight. The product was purified by preparative HPLC using a MeCN/0.1 M ammonium acetate buffer gradient (5/95 to 100/0) as eluent to give the title compound, 12 mg (53%). M/z 753.04.

Example 35

1,1-Dioxo-3,3-dibutyl-5-phenyl-7-methylthio-8-(N-{(R)-α-[2-(S)-2-(carboxy)azetidin-1-ylcarbonyl]benzyl}carbamoylmethoxy)-2,3,4,5-tetrahydro-1,2,5-benzothiadiazepine 1,1-Dioxo-3,3-dibutyl-5-phenyl-7-methylthio-8-(N-{(R)-α-[2-(S)-2-(t-butoxycarbonyl)azetidin-1-ylcarbonyl]benzyl}carbamoylmethoxy)-2,3,4,5-tetrahydro-1,2,5-benzothiadiazepine (Method 22; 27.5 mg, 0.035 mmol) was dissolved in DCM (3 ml) and TFA (1 ml) was added. The reaction was stirred for 1.5 hours. The solvent was evaporated under reduced pressure. The product was lyophilised to give 25 mg of the title compound. M/z 722.92.

Example 36

1,1-Dioxo-3,3-dibutyl-5-phenyl-7-methylthio-8-(N-{(R)-α-[N-{(S)-1-[N-((S)-1-carboxyethyl)carbamoyl]ethyl}carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-(N-{(R)-α-[N-((S)-1-{N-[(S)-1-(t-butoxycarbonyl)ethyl]carbamoyl}ethyl)carbamoyl]benzyl}carbamoylmethoxy)-2,3,4,5-tetrahydro-1,2,5-benzothiadiazepine Method 26; 34 mg, 0.041 mmol) was dissolved in a mixture of DCM:TFA (3:1, 4 ml). The reaction mixture was stirred for 2 hours. The solvent was evaporated under reduced pressure. The product was purified by preparative HPLC using a MeCN/0.1 M ammonium acetate buffer gradient (5/95 to 100/0) as eluent to give the title compound, 23 mg (72%). NMR (500 MHz, CD$_3$OD) 0.81 (bt, 6H), 0.88–1.54 (m, 16H),1.56–1.71 (m, 2H), 2.11 (s, 3H), 3.8–4.2 (m, 2H), 4.33–4.42 (m, 2H), 4.66 (ABq, 2H), 5.55 (s, 1H), 6.61 (s, 1H), 7.07 (t, 1H), 7.22 (brd, 2H), 7.28–7.43 (m, 6H), 7.48 (d, 2H); m/z 782.1.

Example 37

1,1-Dioxo-3,3-dibutyl-5-phenyl-7-methylthio-8-(N-{(R)-α-[N-((R)-1-carboxy-3,3-dimethylbutyl)carbamoyl]benzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-((S)-1-carboxy-3,3-dimethylbutyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 51 mg, 0.080 mmol) was dissolved in 2 ml DMF. t-Butyl 4-methyl D,L-leucinate (Method 27; 23 mg, 0.114 mmol), N-methylmorpholine (18 μl, 0.163 mmol) and TBTU (31 mg, 0.097 mmol) were added successively and the mixture was stirred for 2 hours. One drop of formic acid was added and the mixture was extracted between EtOAc and water. The aqueous phase (pH=3) was washed with EtOAc. The combined organic layers were washed with 5% NaHCO$_3$ and brine and was then dried with Na$_2$SO$_4$ and evaporated to dryness. The intermediate t-butyl ester of the title compound was confirmed. M/z: 823. DCM (2 ml) and TFA (0.5 ml) were added and the solution was stirred overnight. The mixture was concentrated and purified using preparative HPLC on a C8 column (50×250 mm). A step gradient of MeCN (20–50%) in 0.1M ammonium acetate buffer was used as eluent. The two diastereomers separated under these conditions and they were collected and lyophilized separately. The first eluting diastereomer was obtained in 5 mg (16% yield) and the second eluting diastereomer was obtained in 3 mg (10% yield). The absolute configuration was assigned by comparison of NMR-spectra with related compounds and the first eluting diastereomer was found to be the (R,R)-diastereomer and the second eluting diastereomer was the (R,S)-diastereomer. M/z: 767. NMR of the (RR)-diastereomer (400 MHZ): 0.79 (t, 6H), 0.95 (s, 9H), 0.99–1.22 (m, 6H), 1.25–1.39 (m, 2H), 1.40–1.51 (m, 2H), 1.57–1.68 (m, 3H), 1.80 (dd, 1H), 2.08 (s, 3H), 3.95 (brs, 2H), 4.47 (dd, 1H), 4.63 (Abq, 2H), 5.61 (s, 1H), 6.58 (s, 1H), 7.04 (t, 1H), 7.20 (d, 2H), 7.25–7.35 (m, 6H), 7.43–7.47 (m, 2H). And NMR of the (R,S)-diastereomer (400 MHz): 0.7 (s, 9H), 0.79 (t, 6H), 0.99–1.22 (m, 6H), 1.25–1.39 (m, 2H) 1.40–1.51 (m, 3H), 1.55–1.70 (m, 2H), 1.76 (dd, 1H), 2.12 (s, 3H), 3.95 (brs, 2H), 4.35 (dd, 1H), 4.60 (Abq, 2H), 5.54 (s, 1H), 6.60 (s, 1H), 7.04 (t, 1H), 7.20 (d, 2H), 7.24–7.37 (m, 6H), 7.39–7.46 (m, 2H).

Example 38

1,1-Dioxo-3,3-dibutyl-5-phenyl-7-methylthio-8-(N-{(R)-α-[N-((R-1-carboxy-3,3-dimethylbutyl)carbamoyl]-4-hydroxybenzyl}carbamoylmethoxy)-2,3,4,5-tetrahydro-1,2,5-benzothiadiazepine The title compound was prepared by the procedure of Example 37 starting from 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 53 mg, 0.081 mmol). The intermediate t-butyl ester was confirmed. M/z: 839. Only one of the diastereomers were collected from the preparative HPLC purification of the racemic title compound. It was obtained in 4 mg (12%) and was assigned to be the (R,R)-diastereomer from comparison of NMR-data of related compounds. M/z: 783. NMR (400 MHz): 0.79 (t, 6H), 0.95 (s, 9H), 0.99–1.22 (m, 6H), 1.25–1.39 (m, 2H), 1.40–1.51 (m, 2H), 1.56–1.68 (m, 3H), 1.79 (dd, 1H), 2.08 (s, 3H), 3.96 (brs, 2H), 4.47 (dd, 1H), 4.62 (Abq, 2H), 5.47 (s, 1H), 6.58 (s, 1H), 6.73 (d, 2H), 7.04 (t, 1H), 7.19 (d, 2H), 7.24–7.35 (m, 5H).

Example 39

1,1-Dioxo-3,3-dibutyl-5-phenyl-7-methylthio-8-[N-((R)-α-{N-[(R)-1-carboxy-2-(trimethylsilyl)ethyl]carbamoyl}-4-hydroxybenzyl)carbamoylethoxy]-2,3,4,5-tetrahydro-1,2,5-benzothiadiazepine and 1,1-Dioxo-3,3-dibutyl-5-phenyl-7-methylthio-8-[N-(R)-α-{N-[(S)-1-carboxy-2-(trimethylsilyl)ethyl]carbamoyl}-4-hydroxybenzyl)carbamoylmethoxy]-2,3,4,5-tetrahydro-1,2,5-benzothiadiazepine 1,1-Dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine (Example 18; 55 mg, 0.084 mmol) and methyl 3-(trimethylsilyl)alaninate (Method 28; 19 mg, 0.108 mmol) were dissolved in 3.5 ml DMF. N-Methyl morpholine(18 µl, 0.163 mmol) and TBTU (32 mg, 0.101 mmol) were added successively and the mixture was stirred for 2 hours. One drop of formic acid was added and the mixture was then extracted between EtOAc and water. The aqueous phase (pH=3) was washed with EtOAc. The combined organic phases were washed with 1% NaHCO$_3$, brine and was then dried with Na$_2$SO$_4$ and concentrated. The intermediate methyl ester was confirmed. M/z: 813. THF (2 ml), water (2 ml) and LiOH (10 mg, 0.418 mmol) were added and the mixture was stirred over night. The mixture was purified using preparative HPLC on a C8 column (50×100 mm). A gradient from 20 to 50% MeCN in 0.1M ammonium acetate buffer was used as eluent. The two diastereomers were separated under these conditions and were collected separately. Lyophilisation yielded 8 mg (24% yield) of the first eluting diastereomer and 8.4 mg (25% yield) of the second. The absolute configurations were assigned from comparison with NMR-data of related compounds and the first eluting diastereomer was found to be the (R,R)-diastereomer and the second eluting diastereomer was the (R,S)-diastereomer. M/z: 799. NMR of the (R,R)-diastereomer (400 Mz): –0.16 (s, 9H), 0.79 (t, 6H), 0.9–1.22 (m, 8H), 1.25–1.40 (m, 2H), 1.40–1.52 (m, 2H), 1.55–1.68 (m, 2H), 2.11 (s, 3H), 3.95 (brs, 2H), 4.29–4.35 (m, 1H), 4.58 (Abq, 2H), 5.45 (s, 1H), 6.59 (s, 1H), 6.73 (d, 2H), 7.04 (t, 1H), 7.17–7.27 (m, 5H), 7.32 (t, 2H); and of the (R,S)-diastereomer (400 MHz): 0.04 (s, 9H), 0.79 (t, 6H), 1.00–1.22 (m, 8H), 1.25–1.40 (m, 2H), 1.40–1.52 (m, 2H), 1.55–1.68 (m, 2H), 2.08 (s,3H), 3.95 (brs, 2H), 4.40–4.46 (m, 1H), 4.62 (Abq, 2H), 5.49 (s 1H), 6.58 (s, 1H), 6.73 (d, 2H), 7.04 (t, 1H), 7.14–7.36.(m, 7H).

Preparation of Starting Materials

The starting materials for the Examples above are either commercially available or are readily prepared by standard Methods from known materials. For Example, the following reactions are an illustration, but not a limitation, of some of the starting materials used in the above reactions.

Method 1

1,1-Dioxo-3,3-dibutyl-5-phenyl-7-bromo-8-ethoxycarbonylmethoxy-2,3,4,5-tetrahydro-1,2,5-benzothiadiazepine and 1,1-Dioxo-3,3-dibutyl-5-phenyl-7-methylthio-8-ethoxycarbonylmethoxy-2,3,4,5tetrahydro-1,2,5-benzothiadiazepine To a suspension of 1,1-dioxo-3,3-dibutyl-5-phenyl-7-bromo-8-methoxy-2,3,4,5-tetrahydro-1,2,5-benzothiadiazepine (prepared according to WO 98/38182; 0.218 g, 5.65*10$^{-4}$ mol) in DMF (5 ml) was added NaSMe (0.210 g, 2.83 mmol, 95%), and the mixture was stirred for 5 hours at 120° C. The solvent was removed under reduced pressure and the residue was partitioned between EtOAc and 0.5 M HCl. The aqueous layer was extracted twice more with EtOAc and the combined organic extracts were dried (MgSO$_4$) and concentrated. The residue was dissolved in MeCN (7 ml) and ethyl bromoacetate (0.063 ml, 5.65*10$^{-4}$ mol), tetrabutylammonium bromide (0.018 g, 5.65*10$^{-5}$ mol) and sodium carbonate (0.250 g, 2.36 mmol) were added. The mixture was stirred over night at 80° C. The solvent was removed under reduced pressure and the residue was partitioned between EtOAc and 0.5 M HCl. The organic layer was washed with brine, dried (MgSO$_4$) and concentrated. Flash chromatography on silica gel (Hex:EtOAc-6:1) gave the title compounds as colourless oils: 1,1-dioxo-3,3-dibutyl-5-phenyl-7-bromo-8-ethoxycarbonylmethoxy-2,3,4,5-tetrahydro-1,2,5-benzothiadiazepine, 0.187 g (58%). NMR (400 MHz, CDCl$_3$) 0.70–0.80 (m, 6H), 0.90–1.70 (m, 15H), 3.90 (brs, 2H), 4.25 (q, 2H), 4.35 (brs, 1H), 4.65 (s, 2H), 6.95–7.40 (m, 7H); and 1,1-dioxo-3,3-dibutyl-5-phenyl-7-methylthio-8-ethoxycarbonylmethoxy-2,3,4,5-tetrahydro-1,2,5-benzothiadiazepine, 0.024 g (8%). NMR (400 MHz, CDCl$_3$) 0.70–0.85 (m, 6H), 0.90–1.70 (m, 15H), 2.10 (s, 3H), 3.90 (brs, 2H), 4.20 (brs, 1H), 4.25 (q, 2H), 4.65 (s, 2H), 6.55 (s, 1H), 6.95–7.35 (m, 6H).

Method 2

1,1-Dioxo-3,3-dibutyl-5-phenyl-7-bromo-8-carboxymethoxy-2,3,4,5-tetrahydro-1,2,5-benzothiadiazepine To a solution of 1,1-dioxo-3,3-dibutyl-5-phenyl-7-bromo-8-ethoxycarbonylmethoxy-2,3,4,5-tetrahydro-1,2,5-benzothiadiazepine (Method 1; 0.184 g, 3.24*10$^{-4}$ mol) in EtOH (7 ml) was added NaOH (0.052 g, 1.30 mmol) and the mixture was stirred overnight. The solvent was removed under reduced pressure and the residue was partitioned between EtOAc and 0.5 M HCl. The aqueous layer was extracted twice more with EtOAc and the combined organic extracts were washed with brine and concentrated. The crude product was purified by preparative HPLC using an MeCN/ammonium acetate buffer as eluent and freeze-dried to give the title compound in 0.173 g (99%) as a white solid. NMR (400 MHz, CD$_3$OD) 0.70–0.85 (m, 6H), 0.95–1.70 (m, 12H), 3.90 (brs, 2H), 4.50 (s, 2H), 6.90–7.40 (m, 7H).

Method 3

1,1-Dioxo-3,3-dibutyl-5-phenyl-7-methylthio-8-carboxymethoxy-2,3,4,5-tetrahydro-1,2,5-benzothiadiazepine To a solution of 1,1-dioxo-3,3-dibutyl-5-phenyl-7-methylthio-8-ethoxycarbonyl-methoxy-2,3,4,5-tetrahydro-1,2,5-benzothiadiazepine (Method 1; 0.024 g, 4.49*10$^{-5}$ mol) in EtOH (3 ml) was added NaOH (0.007 g, 1.80*10$^{-4}$ mol) and the mixture was stirred over night. The solvent was removed under reduced pressure and the residue was purified by preparative HPLC using an MeCN/ammonium acetate buffer as eluent and freeze-dried. The title compound was obtained in 0.021 g (92%) as a white solid. NMR (400 MHz, CD$_3$OD) 0.70–0.85 (m, 6H), 1.00–1.70 (m, 12H), 2.10 (s, 3H), 3.90 (brs, 2H), 4.55 (s, 2H), 6.60 (s, 1H), 6.90–7.35 (m, 6H).

Method 3

1,1-Dioxo-3,3-dibutyl-5-phenyl-7-methylthio-8-carboxymethoxy-2,3,4,5-tetrahydro-1,2,5-benzothiadiazepine (Alternative Preparation)

1,1-Dioxo-2-(4-methoxybenzyl)-3,3-dibutyl-5-phenyl-7-methylthio-8-(t-butoxycarbonylmethoxy)-2,3,4,5-tetrahydro-1,2,5-benzothiadiazepine (Method 25; 6.902 g, 10.11 mmol) was dissolved in a mixture of TFA (50 ml) and Et$_3$Si (8 ml) and the solution was stirred for 90 min at RT. The solvent was removed under reduced pressure and the residue was dissolved in t-BuOMe (100 ml). The organic phase was washed with water (20 ml) and then extracted three times with diluted NaOH (2×50 ml 0.5M). The combined aqueous extracts were acidified with diluted HCl (70 ml, 1M) (pH 1–2) and were then extracted twice with t-BuOMe (2×50 ml). The ether layer was washed with brine, dried over MgSO$_4$ and concentrated. 4.694 g (92%) of the desire product as brown oil were obtained. NMR (400 MHz, CD$_3$OD): 0.70–0.85 (m, 6H), 1.00–1.25 (m, 6H), 1.25–1.50 (m, 4H), 1.55–1.70 (m 2H), 2.10 (s, 3H), 3.90 (brs, 2H), 4.55 (s, 2H), 6.60 (s, 1H), 6.95–7.35 (m, 6H).

Method 4

(R)-N-Benzyloxycarbonyl-α-[N-(t-butoxycarbonylmethyl)carbamoyl]benzylamine (2R)-{[(Benzyloxy)carbonyl]amino}(phenyl)acetic acid (10 g, 35.0 mmol) and t-butylglycine hydrochloride (6.3 g, 37.4 mmol) was dissolved in DCM (200 ml) with 2,6-lutidine (8.2 ml, 70.4 mmol). After stirring 5 min at 0° C. TBTU (12.4 g, 38.6 mmol) was added and stirring was continued for 1.5 hours at 0° C. and 3.75 hours at room temperature. The reaction mixture was washed with water (2×100 ml), dried (MgSO$_4$) and purified with flash chromatography (DCM:EtOAc 7:1→5:1) to give the title compound (13 g, 94%). NMR (500 MHz, CDCl$_3$): 1.45 (s, 9H), 3.84 (d, 1H), 4.00 (dd, 1H), 5.10 (m, 2H),5.28 (brs, 1H), 6.13 (brs, 1H), 6.23 (brs, 1H), 7.30–7.44 (m, 10H).

Method 5

(R)-α-[N-(t-Butoxycarbonylmethyl)carbamoyl]benzylamine (R)-N-Benzyloxycarbonyl-α-[N-(t-butoxycarbonylmethyl)carbamoyl]benzylamine (Method 4; 12.8 g, 32.2 mmol) was dissolved in EtOH (99%, 200 ml) and toluene (50 ml). Pd/C (10%, 0.65 g) was added and hydrogenation was performed at atmospheric pressure for 5.5 hours at room temperature. The reaction mixture was filtered through diatomaceous earth and the solvents were evaporated to give the title compound (8.4 g, 99%). NMR (600 MHz, CDCl$_3$): 1.45 (s, 9H), 3.93 (m, 2H), 4.54 (s, 1H), 7.31–7.42 (m, 5H), 7.51 (brs, 1H).

Method 6

2-{[(2R)-2-Amino-2-(4-hydroxyphenyl)ethanoyl]amino}ethanesulphonic acid

N-Boc-(D)-4-hydroxyphenylglycine (1.00 g, 3.21 mmol) was dissolved in DMF (5 ml) and tetrabutylammonium taurine (2.36 g, 6.42 mmol) was added together with additionally 5 ml DMF. The resulting suspension was cooled on ice and TBTU (1.24 g, 3.85 mmol) was added. The ice bath was removed after 30 min and the mixture was stirred for 2 hours before it was filtered and concentrated. TFA in DCM (20%, 20 ml) was added and the reaction mixture was stirred over night. Ethanol (20 ml) was added and the solvents evaporated. The crude product was refluxed in ethanol (100 ml) for 1 hour. Filtration yielded the pure title compound as a white solid, 626 mg (71%). NMR (DMSO-d$_6$): 2.4–2.6 (m, 2H), 3.2–3.4 (m, 2H), 4.79 (s, 1H), 6.78 (d, 2H), 7.23 (d, 2H), 8.22 (t, 1H), 8.4 (brs, 3H), 9.7 (s, 1H).

Method 7

4-(1-t-Butoxycarbonyl-1-aminomethyl)phenol

Sulfuric acid (conc, 1 ml) was added to a solution of D-(R)-4-hydroxyphenylglycine (1.0 g, 6.0 mmol) in 1,4-dioxane (8 ml) placed in a Teflon® flask. The flask was cooled to −78° C. and isobutylene (8 g, 142.6 mmol, condensed at −78° C.) was added. The flask was placed in an autoclave at room temperature and stirred for 15 h. The autoclave was cooled on ice before opened. The excess isobutylene was allowed to evaporate and the remaining solution was poured into aqueous NaOH (2M, 20 ml) and was extracted with diethyl ether to remove formed by-product. The aqueous phase was slightly acidified to attain pH=10 using 2M HCl and was extracted with diethyl ether (3×75 ml). The organic phase was washed with brine, dried and concentrated. The obtained product was recrystallized in diethyl ether/hexane. Mass: 0.55 g (41%). NMR (600 MHz, CDCl$_3$) 1.45 (s, 9H), 4.45 (s, 1H), 6.8 (d, 2H), 7.25 (d, 2H); m/z: 224.

Method 8

1,1-Dioxo-3,3-dibutyl-5-phenyl-7-methylthio-8-[N-(R)-α-{N-[(S)-1-(t-butoxycarbonyl)-4-(benzyloxycarbonylamino)butyl]carbamoyl}benzyl)carbamoylmethoxy]-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 53 mg, 0.083 mmol), tert-butyl $N^5$-[(benzyloxy)carbonyl]-L-ornithinate (35 mg, 0.098 mmol), N-methyl morpholine (0.027 m) were dissolved in DCM (5 ml). The mixture was stirred at room temperature for 10 min, where after TBTU (32 mg, 0.10 mmol) was added and the reaction mixture was stirred for 1.5 hours. The solvent was removed under reduced pressure and the residue was purified by chromatography using DCM:EtOAc, 5:1 as eluent to give the title compound 57 mg (72%). M/z=944.7 and 942.7 (M−R)⁻.

Method 9

1,1-Dioxo-3,3-dibutyl-5-phenyl-7-methylthio-8-{N-[(R)-α-(t-butoxycarbonyl)benzyl]carbamoylmethoxy}-2,3,4,5-tetrahydro-1,2,5-benzothiadiazepine 1,1-Dioxo-3,3-dibutyl-5-phenyl-7-methylthio-8-carboxymethoxy-2,3,4,5-tetrahydro-1,2,5-benzothiadiazepine (Method 3; 627 mg, 1.24 mmol) was dissolved in DCM (25 ml), tert-butyl (2R)-amino(phenyl)acetate (308 mg, 1.48 mmol), 2,6-dimethylpyridine (288 μl, 2.47 mmol) and TBTU (477 mg, 1.48 mmol) were added. The mixture was stirred for 3.5 hours. The reaction mixture was evaporated under reduced pressure. The product was purified using an Isolute column (10 g, silica). The product was eluted with a stepwise gradient using DCM:EtOAc 100:0 then 95:5. Approximately 694 mg pure compound was collected. Another fraction was purified a second time using an Isolute column (10 g, silica). The product was eluted with a stepwise gradient using DCM:EtOAc 100:0,95:5 then 90:10. The pure fraction was added to the first fraction yielding 787 mg (91%) of the title compound. NMR (400 MHz, CDCl₃) 0.78 (t, 6H), 0.92–1.12 (m, 4H), 1.12–1.46 (m, 6H), 1.54 (s, 9H), 1.58'1.72 (m, 2H), 2.14 (s, 3H), 3.8–4.05 (m, 2H), 4.32 (brs, NH), 4.56 (ABq, 2H), 5.56 (d, 1H), 6.56 (s, 1H), 7.04 (t, 1H), 7.10 (brd, 2H) 7.24–7.42 (m, 8H), 7.84 (d, NH); m/z 694.7 (M-H)⁻.

Method 10

1,1-Dioxo-3,3-dibutyl-5-phenyl-7-methylthio-8-(N-{(R)-α-[(S)-2-(t-butoxycarbonyl)pyrrolidin-1-ylcarbonyl]benzyl}carbamoylmethoxy-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) and tert-butyl L-prolinate (15 mg, 0.088 mmol) were dissolved in DCM (2ml) and N-methylmorpholine (17.2 μl, 0.156 mmol) and TBTU (45 mg, 0.14 mmol) were added. The reaction mixture was stred for 3 hours then additional tert-butyl L-prolinate (15 mg, 0.088 mmol) was added. The reaction mixture was stirred over night. The reaction mixture was put directly on an Isolute column (2 g, silica). The product was eluted with a stepwise gradient using DCM: EtOAc 100:0, 95:5, 90:10 then 80:20 to give the title compound (41 mg, 66%). M/z 793.2.

Method 11

1,1-Dioxo-3,3-dibutyl-5-phenyl-7-methylthio-8-(N-{(R)-α-[N-(t-butoxycarbonylmethyl)-N-methylcarbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) and tert-butyl N-methylglycinate (15 mg, 0.10 mmol) were dissolved in DCM (2 ml) and N-methylmorpholine (17.2 μl, 0.156 mmol) and TBTU (45 mg, 0.14 mmol) were added. The reaction mixture was stirred for 4 hours. The reaction mixture was put directly on an Isolute column (2 g, silica). The product was eluted with a stepwise gradient using DCM:EtOAc 100:0, 95:5, 90:10 then 80:20 to give the title compound (30 mg, 50%). M/z 767.4.

Method 12

1,1-Dioxo-3,3-dibutyl-5-phenyl-7-methylthio-8-[N-((R)-α-{N-[1-(R)-2-(R)-1-(t-butoxycarbonyl)-1-hydroxy-prop-2-yl]carbamoyl}benzyl)carbamoylmethoxyl]-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol) and tert-butyl (2R,3R)-3-amino-2-hydroxybutanoate (15 mg, 0.086 mmol) were dissolved in DCM (2 ml) and DMF (1 ml) and N-methylmorpholine (17.2 μl, 0.156 mmol) and TBTU (45 mg, 0.14 mmol) were added. The reaction mixture was stirred for 4 hours. The reaction mixture was put directly on an Isolute column (2 g, silica). The product was eluted with a stepwise gradient using DCM:EtOAc 100:0, 95:5, 90:10 then 80:20 to give the title compound (33 mg, 53%). M/z 797.3.

Method 13 t-Butyl N-((2R)-2-{[(benzyloxy)carbonyl]amino}-2-phenylethanoyl-o-(t-butyl)-L-serinate (2R)-{[(Benzyloxy)carbonyl]amino}(phenyl)acetic acid (2.0 g, 7.0 mmol) and t-butyl O-(t-butyl)-L-serinate (2.0 g, 7.9 mmol) and 2.6-lutidine were dissolved in DCM (30 ml). After stirring 5 min at 0° C. TBTU (2.5 g, 7.8 mmol) was added and stirring was continued 30 min at 0° C. and 4 h. at room temperature. The reaction mixture was washed with water (2×100 ml), dried and purified with flash chromatography (DCM) to give the title compound (3.3 g, 97%). NMR (300 MHz): 1.05 (s, 9H), 1.45 (s, 9H), 3.4–3.8 (m, 2H) 4.5 (brs, 1H), 4.85(s, 2H), 5.1 (s, 2H), 5.4 (s, 1H), 7.25–7.5 (m, 10 H).

Method 14 t-Butyl N-[(2R)-2-amino-2-phenylethanoyl]-o-(t-butyl)-L-serinate t-Butyl N-((2R)-2-{[(benzyloxy)carbonyl]amino}-2-phenylethanoyl)-o-(t-butyl)-L-serinate (Method 13; 3.3 g, 6.8 mmol) was dissolved in EtOH (95%, 30 ml) and a catalytic amount of Pd/C (5%)(50% in water) was added and hydrogenation was performed at atmospheric pressure for 3 h. at room temperature. The reaction mixture was filtered through diatomaceous earth and the solvent was evaporated to give the title compound (2.35 g, 98%). NMR (500 MHz): 1.1 (s, 9H), 1.45 (s, 9H), 3.45–3.8 (m, 2H), 4.5 (t, 1H), 4.55 (s 1H), 4.85 (s, 2H), 7.3–7.5 (m, 5H).

Method 15

1,1-Dioxo-2-(4-methoxybenzyl)-3,3-dibutyl-5-phenyl-7-methyl-8-methoxy-2,3,4,5-tetrahydro-1,2,5-benzothiadiazepine To a cooled solution (−78° C.) of 1,1-dioxo-2-(4-methoxybenzyl)-3,3dibutyl-5-phenyl-7-bromo-8-methoxy-2,3,4,5-tetrahydro-1,2,5-benzothiadiazepine (Method 23; 2.10 g, 3.41 mmol) in THF (50 ml) was added dropwise a solution of n-BuLi (2.35 ml, 3.75 mmol, 1.6 M in hexane). After stirring at −78° C. for 20 minutes, MeI (2.42 g, 17.1 mmol) was added. The mixture was stirred at −78° C. for 10 minutes and at room temperature for 18 hours. Diethyl ether (50 ml) was added and the organic phase was washed with 10% $NH_4Cl$ (aq, 50 ml) and brine (50 ml). After drying, filtration and concentration the crude product was subjected to flash chromatography (Hexane:EtOAc—95:5) to give 0.4 gram (21%) of the title product as colourless oil. NMR (300 MHz, $CDCl_3$): 0.60–0.70 (m, 6H), 0.70–0.90 (m, 4H), 0.90–1.35 (m, 8H), 2.00 (s, 3H), 3.70 (s, 3H), 3.80 (s, 3H), 4.00–4.20 (m, 2H), 4.35–4.60 (m, 2H), 6.65–6.85 (m, 3H), 6.90–7.10 (m, 3H), 7.15–7.30 (m, 5H).

Method 16

1,1-Dioxo-3,3-dibutyl-5-phenyl-7-methyl-8-carboxymethoxy-2,3,4,5-tetrahydro-1,2,5-benzothiadiazepine To a solution (0° C.) of trifluoroacetic acid (30 ml) and triethylsilane (1.03 g, 8.85 mmol) was added a solution of 1,1-dioxo-2-(4-methoxybenzyl)-3,3-dibutyl-5-phenyl-7-methyl-8-methoxy-2,3,4,5-tetrahydro-1,2,5-benzothiadiazepine (Method 15; 0.92 g, 1.77 mmol) in DCM (2 ml). The reaction mixture was stirred at room temperature for 30 minutes. After concentration of the reaction mixture, the residue was dissolved in diethyl ether (50 ml) and washed with water (25 ml) and sodium bicarbonate (10%, 25 ml). After drying, filtration and concentration the crude product was subjected to flash chromatography on silica gel (Hexane:EtOAc—90:10) to give 0.58 g of a grey solid. To a solution (0° C.) of this solid in dichloromethane (30 ml) was added dropwise $BBr_3$ in DCM (1M in DCM, 10.2 ml, 10.2 mmol). The reaction mixture was stirred at room temperature for 45 minutes and then it was washed with sodium bicarbonate (10%, 25 ml) and water (25 ml). After drying, filtration and concentration the crude product (0.55 g, grey solid) was dissolved in MeCN (30 ml). The solution was added $K_2CO_3$ (0.22 g, 1.58 mmol) and tetra-n-butyl ammonium bromide (10 mg) followed by ethyl bromoacetate (0.25 g, 1.51 mmol). The reaction mixture was stirred at 80° C for 1.5 h and then evaporated under reduced pressure. The residue was dissolved in EtOAc (50 ml) and washed with $NH_4Cl$ (aq, 10%) and brine. After drying, filtration and concentration the crude product was subjected to flash chromatography (Hex:EtOAc 9:1–8:2) to afford 0.58 g of an off-white solid. The solid was dissolved in THF:$H_2O$ (4:1, 25ml) and LiOH (0.097 g, 2.31 mmol) was added. The reaction mixture was stirred at room temperature for 40 min. The mixture was evaporated under reduced pressure, dissolved in water (50 ml) and acidified with 1M HCl. The aqueous layer was extracted 2× with diethyl ether. Evaporation of the solvent under reduced pressure gave 0.46 g (55%) of the title compound. NMR (300 MHz, acetone-$d_6$); 0.70–0.90 (m, 6H), 0.95–1.80 (m, 12H), 2.15 (s, 3H), 3.85–4.15 (m, 2H), 4.85 (s, 2H), 6.00 (s, 1H), 6.80 (s, 1H), 6.90–7.05 (m, 1H), 7.10–7.45 (m, 5H).

Method 17

(R)-N-Benzyloxycarbonyl-α-carboxy-4-hydroxybenzylamine (R)-p-Hydroxyphenylglycine (5.00 g, 29.9 mmol) was mixed with water (50 ml). Sodium bicarbonate (6.3 g, 75.0 mmol) was added to the slurry and a white suspension was the result after 10 min stirring. Benzyl chloroformate (5.1 ml, 33.9 mmol) was added from a dropping funnel over 20 min and the mixture was stirred vigorously. After 2 h, water (300 ml) was added and the suspension was extracted with ether (200 ml). The white solid did not dissolve and more water and ether were added. LC/MS indicated that the solid was product. The clear part of the aqueous phase was collected and acidified upon a white precipitate was formed. This was left over the weekend and was then filtered off. The remaining aqueous phase containing undissolved material was acidified as well and was extracted with EtOAc (3×). Also here a precipitate remained between the phases. This was collected with the organic layer. The EtOAc phase was evaporated. Toluene was added 2× to remoye water. The two fractions of white solid were added together and recrystallized in DCM (200 ml). The cooled mixture was filtered and 4.77 g (53%) of white solid were obtained. NMR (400 MHz, DMSO-$d_6$): 5.00 (1H, d), 5.00 (2H, s), 6.70 (2H, d), 7.05–7.50 (7H, m), 7.90 (1H, d)

Method 18

(R)-N-Benzyloxycarbonyl-α-{N-[(S)-1-(t-butoxycarbonyl)propyl]carbamoyl}-4-hydroxybenzylamine A solution of (R)-N-benzyloxycarbonyl-α-carboxy-4-hydroxybenzylamine (Method 17; 2.00 g, 6.64 mmol), (2S)-2-amino butanoic acid t-butyl ester (1.30 g, 6.64 mmol) and N-methylmorpholine (2.0 g, 19.8 mmol) in DCM (30 ml) was stirred at RT for 5 min, after which TBTU (2.60 g, 8.10 mmol) was added. The reaction mixture was stirred at ambient temperature overnight. The solvent was removed under reduced pressure and the residue was purified by flash chromatography on silica gel DCM:Acetone—60:40). The product was crystallized from toluene (20 ml) giving 1.85 g of the desired product as a white solid. NMR (400 MHz): 0.80 (3H, t), 1.45 (9H, s), 1.50–1.80 (2H, m), 4.10–4.20 (1H, m), 5.05 (1H, d(AB)), 5.15 (1H, d(AB)), 6.75 (2H, d), 7.20–7.40 (7H, m).

Method 19

(R)-α-{N-[(S)-1-(t-Butoxycarbonyl)propyl]carbamoyl}-4-hydroxybenzylamine

A mixture of (R)-N-Benzyloxycarbonyl-α-{N-[(S)-1-(t-butoxycarbonyl)propyl]carbamoyl}-4-hydroxybenzylamine Method 18; 1.80 g, 4.07 mmol) and Pd/C (0.2 g, 5%) in ethanol (30 ml, 95%) was stirred under hydrogen gas at room temperature for 2 hours. The reaction mixture was filtered through silica gel (2 g) and concentrated. The residue was dissolved in acetone (20 ml) and methanesulphonic acid (0.40 g, 4.16 mmol) was added. No crystallization was obtained and the solvent was removed under reduced pressure. The crude product was purified by preparative HPLC using a gradient of 20–50% MeCN in 0.1M ammonium acetate buffer as eluent. The title compound was obtained in 0.350 g (28%) as a white solid. NMR (400 MHz, DMSO-$d_6$): 0.75 (3H, t), 1.40 (9H, s), 1.50–1.75 (2H, m), 2.70 (1H, s), 4.00–4.10 (1H, m), 4.30 (1H, s), 6.65 (2H, d), 7.15 (2H, d), 8.15 (1H, d).

Method 20

1,1-Dioxo-3,3-dibutyl-5-phenyl-7-methylthio-8-(N-{(R)-α-[N-((S)-1-{N-[(S)-2-(t-butoxy)-1-(t-butoxycarbonyl)ethyl]carbamoyl}propyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine (Example 6, 15 mg, 0.021 mmol), tert-butyl O-(tert-butyl)-L-serinate hydrochloride (5.4 mg, 0.021 mmol) and N-methylmorpholine (4.6 μl, 0.042 mmol) was dissolved in DMF (1 ml). TBTU (12.5 mg, 0.039 mmol) was added and the mixture was stirred for one hour. tert-butyl O-(tert-butyl)-L-serinate hydrochloride (0.8 mg, 0.0031 mmol) was added and the mixture was stirred for a couple of minutes. The solvent was evaporated under reduced pressure and co-evaporated a few times with toluene. The product was purified using a pre-packed ISOLUTE column (Silica, 2 g) and eluted with a stepwise gradient using DCM:EtOAc 100:0 (10 ml) 95:5 (10 ml) 90:10 (10 ml) 80:20 (10 ml), to give 14 mg of the title compound. M/z 924.7.

Method 21

1,1-Dioxo-3,3-dibutyl-5-phenyl-7-methylthio-8-(N-{(R)-α-[2-(S)-2-(methoxycarbonyl)-4-(R)-4-(hydroxy)-pyrrolidin-1-ylcarbonyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 54 mg, 0.084 mmol), methyl (4R)-4-hydroxy-L-prolinate hydrochloride (18.4 mg, 0.10 mmol) and N-methylmorpholine (13.9 μl, 0.13 mmol) was dissolved in DMF (2 ml). TBTU (32.5 mg, 0.101 mmol) was added and the mixture was stirred for three hours. The solvent was evaporated under reduced pressure. The product was purified two times using a pre-packed ISOLUTE column (Silica, 2 g) and eluted with a stepwise gradient using DCM:EtOAc 100:0, 95:5, 90:10, 80:20 and 60:40, to give 23 mg of the title compound. M/z 767.0.

Method 22

1,1-Dioxo-3,3-dibutyl-5-phenyl-7-methylthio-8-(N-{(R)-α-[2-(S)-2-(t-butoxycarbonyl)azetidin-1-ylcarbonyl]benzyl}carbamoylmethoxy)-2,3,4,5-tetrahydro-1 2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 50 mg, 0.078 mmol), tert-butyl (2S)-azetidine-2-carboxylate (17.4 mg, 0.111 mmol) and N-methylmorpholine (10.3 μl, 0.094 mmol) was dissolved in DMF (2 ml). TBTU (30 mg, 0.094 mmol) was added and the mixture was stirred for four hours. The solvent was evaporated under reduced pressure. The product was purified using a pre-packed ISOLUTE column (Silica, 2 g) and eluted with a stepwise gradient using DCM:EtOAc 100:0, 95:5, 90:10, 80:20, to give 27.5 mg of the title compound. M/z 777.6 M-H)⁻.

Method 23

1,1-Dioxo-2-(4-methoxybenzyl)-3,3-dibutyl-5-phenyl-7-bromo-8-methoxy-2,3,4,5-tetrahydro-1,2,5-benzothiadiazepine To a solution of 1,1-dioxo-3,3-dibutyl-5-phenyl-7-bromo-8-methoxy-2,3,4,5-tetrahydro-1,2,5-benzothiadiazepine (prepared according to WO 98/38182; 0.200 g, 0.404 mmol) in MeCN (5 ml) where added p-methoxybenzyl chloride (0.066 ml, 0.486 mmol), CsI (0.010 g, 0.038 mmol) and Cs2CO3 (0.263 g, 0.807 mmol) and the mixture was stirred at 60° C. for 4 h. The solvent was removed under reduced pressure and the residue was partitioned between EtOAc and 0.5M HCl (aq). The organic layer was washed with brine, dried over MgSO4 and concentrated. The residue was filtered through silica gel (DCM:EtOAc-9:1) to give the title compound in 0.257 g (~quant) as an off-white solid. NMR (400 MHz, CDCl$_3$): 0.60–0.75 (m, 6H), 0.75–1.20 (m, 8H), 1.25–1.45 (m, 2H), 1.80–2.00 (m, 2H), 3.80 (s, 3H), 3.90 (s, 3H), 4.05–4.30 (m, 2H), 4.45–4.65 (m, 2H), 6.70–7.45 (m, 11H).

Method 24

1,1-Dioxo-2-(4-methoxybenzyl)-3,3-dibutyl-5-phenyl-7-methylthio-8-hydroxy-2,3,4,5-tetrahydro-1,2,5-benzothiadiazepine NaSMe (0.150 g, 2.03 mmol, 95%) was added to a solution of 1,1-dioxo-2-(4-methoxybenzyl)-3,3-dibutyl-5-phenyl-7-bromo-8-methoxy-2,3,4,5-tetrahydro-1,2,5-benzothiadiazepine (Method 23; 0.249 g, 0.404 mmol) in DMF (5 ml). The mixture was stirred at RT for 2 h, after which the temperature was raised to 80° C. and more NaSMe (0.090 g, 1.22 mmol) was added. After 20 h at 80° C. the mixture was added water (5 ml) and 1M HCl (aq) (ph~4). The solution was extracted three times with Et₂O and the combined organic layers was washed with brine, dried over MgSO$_4$ and concentrated. The crude product was purified by flash chromatography on silica gel (Hex:EtOAc—4:1), which gave the title compound in 0.188 g (82%) as tan solid. NMR (500 MHz, CDCl$_3$): 0.60–0.75 (m, 6H), 0.75–1.20 (m, 8H), 1.25–1.40 (m, 2H), 1.80–2.00 (m, 2H), 2.20 (s, 3H), 3.80 (s, 3H), 4.20 (brs, 2H), 4.50 (brs, 2H), 6.05 (brs, 1H), 6.75–6.85 (m, 3H), 7.00–7.10 (m, 3H), 7.20–7.35 (m, 4H), 7.50 (s, 1H).

Method 25

1,1-Dioxo-2-(4-methoxybenzyl-3,3-dibutyl-5-phenyl-7-methylthio-8-(t-butoxycarbonylmethoxy)-2,3,4,5-tetrahydro-1,2,5-benzothiadiazepine A solution of 1,1-dioxo-2-(4-methoxybenzyl)-3,3-dibutyl-5-phenyl-7-methylthio-8-hydroxy-2,3,4,5-tetrahydro-1,2,5-benzothiadiazepine (Method 24; 4.487 g, 7.889 mmol) in MeCN (100 ml) was added t-butyl bromide (0.262 g, 0.813 mmol), t-butyl bromoacetate (1.46 ml, 9.880 mmol)

and potassium carbonate (anhydrous, 3.28 g, 23.7 mmol) in this order. The mixture was heated to 55° C. for 2.5 h, after which it was cooled to RT and left stirring over night. The solvent was evaporated until a yellowish slurry remained, which was extracted between diethyl ether (150 ml) and water (100 ml). The aqueous phase was washed with ether (100 ml) and the combined ether layers were washed with 0.1M KHSO$_4$ (aq, 100 ml), brine (100 ml) and were dried The ether was removed under reduced pressure and the beige solid obtained was dried under reduced pressure for 4 h (5.355 g, 99%). NMR (400 MHz, CDCl$_3$): 0.60–1.25 (m, 14H), 1.25–1.40 (m, 2H), 1.50 (s, 9H), 1.75–2.00 (m, 2H), 2.10 (s, 3H), 3.80 (s, 3H), 4.20 (brs, 2H), 4.50 (brs, 2H), 4.60 (s, 2H), 6.45 (s, 1H), 6.75–6.85 (m, 2H), 7.00–7.15 (m, 3H), 7.20–7.40 (m, 5H).

Method 26

1,1-Dioxo-3,3-dibutyl-5-phenyl-7-methylthio-8-(N-{(R)-α-[N-((S)-1-{N-[(S)-1-(t-butoxycarbonyl)ethyl]carbamoyl}ethyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl)carbamoylmethoxy]-2,3,4,5-tetrahydro-1,2,5-benzothiadiazepine (Example 25; 58 mg, 0.091 mmol), tert-butyl L-alanyl-L-alaninate hydrochloride (27.5 mg, 0.11 mmol) and N-methylmorpholine (20 µl, 0.18 mmol) was dissolved in DMP (2 ml). TBTU (35 mg, 0.18 mmol) was added and the mixture was stirred for 2–3 hours. The solvent was evaporated under reduced pressure. The product was purified using a pre-packed ISOLUTE column (Silica, 2 g) and eluted with a stepwise gradient using DCM:EtOAc 100:0, 95:5, 90:10 and 80:20 to give 34 mg (45%) of the title compound. M/z 838.5.

Method 27 tert-Butyl 4-methylleucinate

4-Methylleucine (500 mg, 3.44 mmol) was suspended in 10 ml t-butyl acetate. Perchloric acid (0.2 ml, 3.49 mmol) was added and the flask was stopped with a septum and stirred over night. Analysis was performed using TLC DCM:MeOH, 9:1; staining with a ninhydrine/EtOH solution). The solution was poured into a flask containing 30 ml EtOAc and 30 ml 5% Na$_2$CO$_3$. The aq-layer turned acidic and 2M NaOH was added until pH was approximately 7. The phases were separated and the aq-phase was washed with 2×30 ml EtOAc. The combined organic phases were washed with brine, dried with Na$_2$SO$_4$ and evaporated. A oil was obtained which was co-evaporated with toluene and then with diethyl ether before being placed under vacuum for two days. Mass 665 mg (96% yield). NMR (CDCl$_3$): 1.0 (s, 9H), 1.5 (s, 9H), 1.65–1.95 (m, 2H), 3.82 (t, 1H).

Method 28

Methyl 3-(trimethylsilyl)alaninate

3-Trimethylsilyl alanine (J. Organomet. Chem., 628, (2001), 183–194; 19 mg, 0.118 mmol) was mixed with 3 ml BF$_3$-MeOH (14%, 3.7 mmol) in a sealed tube and heated to 70° C. Analysis was performed using TLC (MeOH:DCM 1:9, stained w. ninhydrine in ethanol). The mixture was heated for 3 h and was then cooled to ambient temperature. The mixture was poured into a mixture of 3 ml EtOAc and 2 ml water containing Na$_2$CO$_3$. More Na$_2$CO$_3$ (5%-aq) was added until pH ca 7. The aqueous phase was washed with EtOAc (2×3 ml). The combined organic layers were washed with brine (1 ml), dried with Na$_2$SO$_4$ and evaporated. The product was obtained as a white film. Mass: 19 mg (92% yield). NMR (CDCl$_3$): 0.1 (s, 9H), 1.2–1.4 (m, 2H), 3.8 (s, 3H), 4.2 (brs, 1H).

What is claim is:

1. A compound of formula (I):

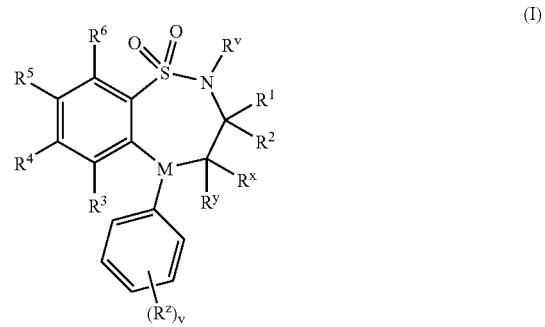

wherein:

$R^v$ is selected from hydrogen or $C_{1-6}$alkyl;

One of $R^1$ and $R^2$ are selected from hydrogen, $C_{1-6}$alkyl or $C_{2-6}$alkenyl and the other is selected from $C_{1-6}$alkyl or $C_{2-6}$alkenyl;

$R^x$ and $R^y$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

M is selected from —N— or —CH—;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0–5;

one of $R^4$ and $R^5$ is a group of formula (IA):

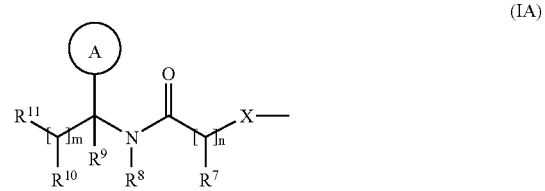

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$, wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(O$R^c$)(O$R^d$), —P(O)(OH)(O$R^c$), —P(O)(OH)($R^d$) or —P(O)(O$R^c$)($R^d$) wherein $R^c$ and $R^d$ are independently selected from $C_{1-6}$allkyl; or $R^{11}$ is a group of formula (IB) or (IC):

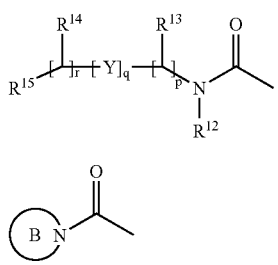

$R^{19}$, $R^{20}$, $R^{24}$ and $R^{26}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$ alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, carbocyclyl, heterocyclyl, benzyloxycarbonylamino, ($C_{1-4}$alkyl)$_3$silyl, sulpho, sulphino, amidino, phosphono, —P(O)(O$R^a$)(O$R^b$), —P(O)(OH)(O$R^a$), —P(O)(OH)($R^a$) or —P(O)(O$R^a$)($R^b$), wherein $R^a$ and $R^b$ are independently selected from $C_{1-6}$alkyl; wherein $R^{19}$, $R^{20}$, $R^{24}$ and $R^{26}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, tifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{23}$ is carboxy, sulpho, sulphino, phosphono, —P(O)(O$R^g$)(O$R^h$), —P(O)(OH)(O$R^g$), —P(O)(OH)($R^g$) or —P(O)(O$R^g$)($R^h$) wherein $R^g$ and $R^h$ are independently selected from $C_{1-6}$alkyl;

$R^{25}$ is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)carbamoyl, benzyl, benzyloxycarbonyl, benzoyl and phenylsulphonyl;

wherein "heteroaryl" is a totally unsaturated, mono or bicyclic ring containing 3–12 atoms of which at least one atom is chosen from nitrogen, sulphur or oxygen, which may, unless otherwise specified, be carbon or nitrogen linked;

wherein a "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a $CH_2$ group can optionally be replaced by a C(O) or a ring sulphur atom may be optionally oxidised to form the S oxides; and wherein a "carbocyclyl" is a saturated, partially saturated or unsaturated, mono or bicyclic carbon ring that contains 3–12 atoms; wherein a $CH_2$ group can optionally be replaced by a C(O);

or a pharmaceutically acceptable salt thereof.

2. A compound of formula (I) as claimed in claim 1 wherein $R^v$ is hydrogen or a pharmaceutically acceptable salt thereof.

3. A compound of formula (I) as claimed in claim 1 wherein $R^1$ and $R^2$ are both butyl or a pharmaceutically acceptable salt thereof.

4. A compound of formula (I) as claimed in claim 1 wherein $R^x$ and $R^y$ are both hydrogen or a pharmaceutically acceptable salt thereof.

5. A compound of formula (I) as claimed in claim 1 wherein M is —N— or a pharmaceutically acceptable salt thereof.

6. A compound of formula (I) as claimed in claim 1 wherein v is 0 or a pharmaceutically acceptable salt thereof.

7. A compound of formula (I) as claimed in claim 1 wherein $R^3$ and $R^6$ are hydrogen or a pharmaceutically acceptable salt thereof.

8. A compound of formula (I) as claimed in claim 1 wherein $R^4$ is bromo, methyl or methylthio or a pharmaceutically acceptable salt thereof.

9. A compound of formula (I) as claimed in claim 1 wherein $R^5$ is a group of formula (IA) (as depicted in claim 1) wherein:

X is —O—;

Ring A is phenyl optionally substituted by one or more substituents selected from $R^{17}$;

n is 1;

$R^7$ is hydrogen;

$R^8$ is hydrogen;

$R^9$ is hydrogen;

m is 0;

$R^{11}$ is carboxy, a group of formula (IB) (as depicted above) or a group of formula (IC) (as depicted above) wherein:

$R^{12}$ is hydrogen or $C_{1-4}$alkyl;

p is 1 or 2;

$R^{13}$ is hydrogen or $C_{1-6}$alkyl optionally substituted by $R^{20}$ wherein $R^{20}$ is hydroxy, carbamoyl, amino, benzyloxycarbonylamino, $C_{1-4}$alkylS(O)$_a$ wherein a is 0 or ($C_{1-4}$ alkyl)$_3$silyl;

$R^{14}$ is hydrogen or hydroxy or $C_{1-6}$alkyl; wherein $R^{14}$ may be optionally substituted by one or more substituents selected from $R^{20}$;

Y is —N($R^n$)C(O)— wherein $R^n$ is hydrogen;

q is 0 or 1;

r is 0 or 1;

$R^{15}$ is carboxy or sulpho;

$R^{17}$ is hydroxy; and
$R^{20}$ is selected from hydroxy;
Ring B is pyrrolidin-1-yl or azetidinyl substituted on carbon by one group selected from $R^{23}$, and optionally additionally substituted on carbon by one or more $R^{24}$; wherein $R^{23}$ is carboxy and $R^{24}$ is hydroxy;
or a pharmaceutically acceptable salt thereof.

10. A compound of formula (I) as claimed in claim 1 wherein:
$R^v$ is hydrogen;
$R^1$ and $R^2$ are both butyl;
$R^x$ and $R^y$ are both hydrogen;
M is —N—;
v is 0;
$R^3$ and $R^6$ are hydrogen;
$R^4$ is bromo, methyl or methylthio; and
$R^5$ is N-{(R)-α-[N-(carboxymethyl)carbamoyl]benzyl}carbamoylmethoxy, N-{(R)-α-[N-(2-sulphoethyl)carbamoyl]-4-hydroxybenzyl}carbamoylmethoxy, N-{(R)-α-[N-((S)-1-carboxy-2-hydroxyethyl)carbamoyl]benzyl}carbamoylmethoxy, N-{(R)-α-[N-((S)-1-carboxyethyl) carbamoyl]benzyl}carbamoylmethoxy, N-{(R)-α-[N-((S)-1-carboxypropyl)carbamoyl]benzyl}carbamoylmethoxy, N-{(R)-α-[N-((R)-1-carboxy-2-methylthio-ethyl)carbamoyl]benzyl}carbamoylmethoxy, N-{(R)-α-[N-((S)-1-carboxy-2-carbamoyl-ethyl)carbamoyl]benzyl}carbamoylmethoxy, N-{(R)-α-[N-(2-sulphoethyl)carbamoyl]-4-hydroxybenzyl}carbamoylmethoxy, N-{(R)-α-[N-(carboxymethyl)carbamoyl]-4-hydroxybenzyl}carbamoylmethoxy, N-{(R)-α-[N-((S)-1-carboxyethyl)carbamoyl]-4-hydroxybenzyl}carbamoylmethoxy, N-{(R)-α-[N-((S)-1-carboxy-2-hydroxyethyl) carbamoyl]-4-hydroxybenzyl}carbamoylmethoxy, N-{(R)-α-[N-(2-sulphoethyl)carbamoyl]benzyl}carbamoylmethoxy, N-{(R)-α-[N-((S)-1-carboxy-2-(R)-hydroxypropyl) carbamoyl]benzyl}carbamoylmethoxy, N-{(R)-α-[N-((S)-1-carboxy-2-methylpropyl)carbamoyl]benzyl}carbamoylmethoxy, N-{(R)-α-[N-((S)-1-carboxy-3-methylbutyl)carbamoyl]benzyl}carbamoylmethoxy, N-{(R)-α-[N-(1-(S)-1-carboxy-2-(S)-2-methylbutyl)carbamoyl]benzyl}carbamoylmethoxy, N-((R)-α-carboxy-4-hydroxybenzyl)carbamoylmethoxy, N-{(R)-α-[N-((S)-1-carboxy-4-aminobutyl)carbamoyl]benzyl}carbamoylmethoxy, N-((R)-α-{N-[(S)-1-carboxy-4-(benzyloxycarbonylamino)butyl]carbamoyl}benzyl)carbamoylmethoxy, N-[(R)-α-((S)-2-carboxypyrrolidin-1-ylcarbonyl)benzyl]carbamoylmethoxy, N-{(R)-α-[N-(carboxymethyl)-N-methylcarbamoyl]benzyl}carbamoylmethoxy, N-{(R)-α-[N-(1-(R)-2-(R)-1-carboxy-1-hydroxyprop-2-yl)carbamoyl]benzyl}carbamoylmethoxy, N-{(R)-α-[N-(sulphomethyl)carbamoyl]benzyl}carbamoylmethoxy, N-((R)-α-carboxybenzyl)carbamoylmethoxy, N-{(R)-α-[N-((S)-1-carboxy-2-(R)-hydroxypropyl)carbamoyl]-4-hydroxybenzyl}carbamoylmethoxy, N-{(R)-α-[N-((S)-1-carboxy-2-methylpropyl)carbamoyl]-4-hydroxybenzyl}carbamoylmethoxy, N-{(R)-α-[N-((S)-1-carboxybutyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-((R)-1-carboxy-2-methylthio-ethyl)carbamoyl]-4-hydroxybenzyl}carbamoylmethoxy, N-{(R)-α-[N-((S)-1-carboxypropyl)carbamoyl]-4-hydroxybenzyl}carbamoylmethoxy, N-{(R)-α-[N-{(S)-1-[N-((S)-2-hydroxy-1-carboxyethyl)carbamoyl]propyl}carbamoyl]benzyl}carbamoylmethoxy, N-{(R)-α-[2-(S)-2-(carboxy)-4-(R)-4-(hydroxy)pyrrolidin-1-ylcarbonyl]benzyl}carbamoylmethoxy, N-{(R)-α-[2-(S)-2-(carboxy)azetidin-1-ylcarbonyl]benzyl}carbamoylmethoxy, N-{(R)-α-[N-{(S)-1-[N-((S)-1-carboxyethyl)carbamoyl]ethyl}carbamoyl]benzyl}carbamoylmethoxy, N-{(R)-α-[N-((R)-1-carboxy-3,3-dimethylbutyl)carbamoyl]benzyl}carbamoylmethoxy, N-{(R)-α-[N-((S)-1-carboxy-3,3-dimethylbutyl)carbamoyl]benzyl}carbamoylmethoxy, N-{(R)-α-[N-((R)-1-carboxy-3,3-dimethylbutyl)carbamoyl]-4-hydroxybenzyl}carbamoylmethoxy, N-((R)-α-{N-[(S)-1-carboxy-2-(trimethylsilyl)ethyl]carbamoyl}-4-hydroxybenzyl)carbamoylmethoxy or N-((R)-α-{N-[(R)-1-carboxy-2-(trimethylsilyl)ethyl]carbamoyl}-4-hydroxybenzyl)carbamoylmethoxy;
or a pharmaceutically acceptable salt thereof.

11. A compound of formula (I) as claimed in claim 1 selected from:
1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxybutyl) carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]
benzyl}carbamoylmethoxy)-2,3,4,5-tetrahydro-1,2,5-
benzothiadiazepine; and 1,1-dioxo-3,3-dibutyl-5-phenyl-7-methylthio-8-(N-{(R)-
α-[N-((S)-1-carboxy-2-methylpropyl)carbamoyl]
benzyl}carbamoylmethoxy)-2,3,4,5-tetrahydro-1,2,5-
benzothiadiazepine;

or a pharmaceutically acceptable salt thereof.

12. A process for preparing a compound of formula (I) as claimed in claim 1 or a pharmaceutically acceptable salt thereof which process comprises of:

Process 1): for compounds of formula (I) wherein X is —O—, —NR$^a$ or —S—; reacting a compound of formula (IIa) or (IIb):

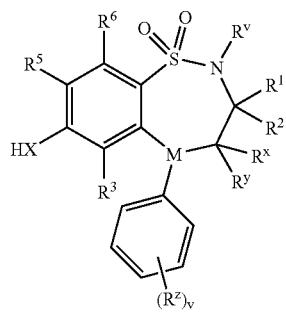
(IIa)

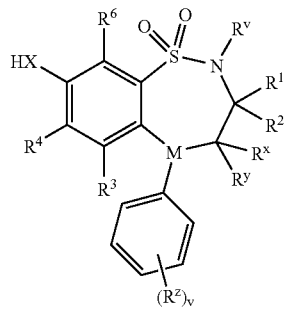
(IIb)

with a compound of formula (III):

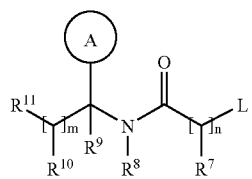
(III)

wherein L is a displaceable group;

Process 2): reacting an acid of formula (IVa) or (IVb):

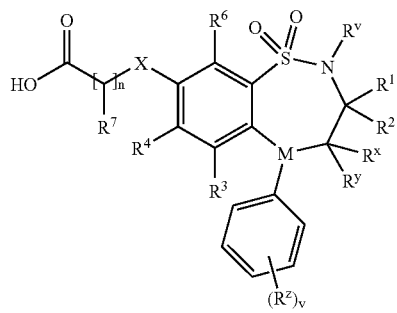
(IVa)

-continued

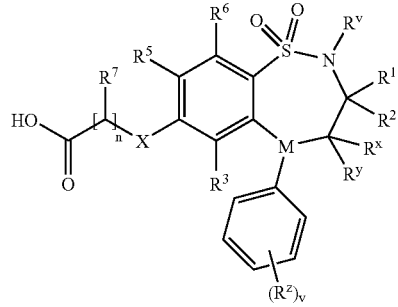
(IVb)

or an activated derivative thereof; with an amine of formula (V):

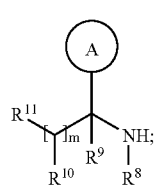
(V)

Process 3): for compounds of formula (I) wherein R$^{11}$ is a group of formula (IB); reacting a compound of formula (I) wherein R$^{11}$ is carboxy with an amine of formula (VI):

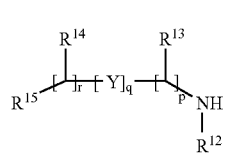
(VI)

Process 4) for compounds of formula (I) wherein one of R$^4$ and R$^5$ are independently selected from C$_{1-6}$alkylthio optionally substituted on carbon by one or more R$^{17}$; reacting a compound of formula (VIIa) or (VIIb):

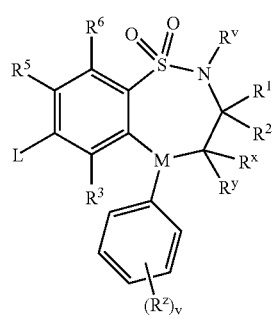
(VIIa)

-continued

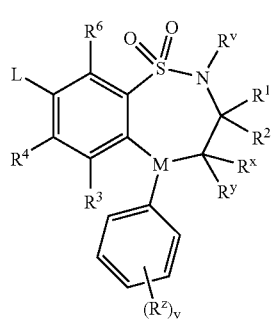
(VIIb)

wherein L is a displaceable group; with a thiol of formula (VIII):

$$R^m{-}H \quad (VIII)$$

wherein $R^m$ is $C_{1-6}$alkylthio optionally substituted on carbon by one or more $R^{16}$;

Process 5): for compounds of formula (I) wherein $R^{11}$ is carboxy, deprotecting a compound of formula (IXa):

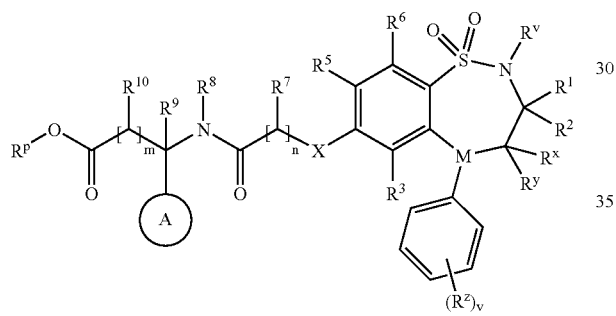
(IXa)

or (IXb):

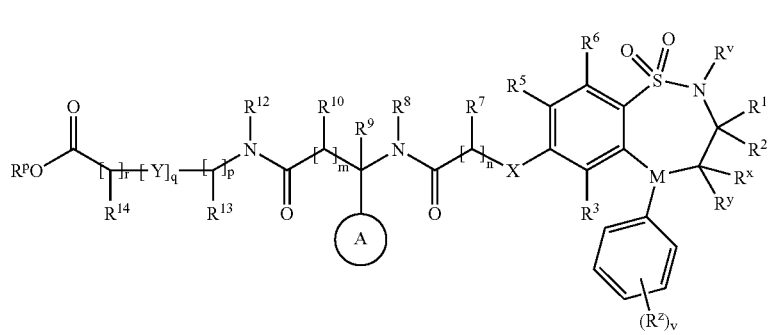
(IXb)

wherein $R^p$ together with the —OC(O)— group to which it is attached forms an ester;

Process 6): for compounds of formula (I) wherein $R^{11}$ is a group of formula (IB) and $R^{15}$ is carboxy, deprotecting a compound of formula (Xa):

(Xa)

or (Xb):

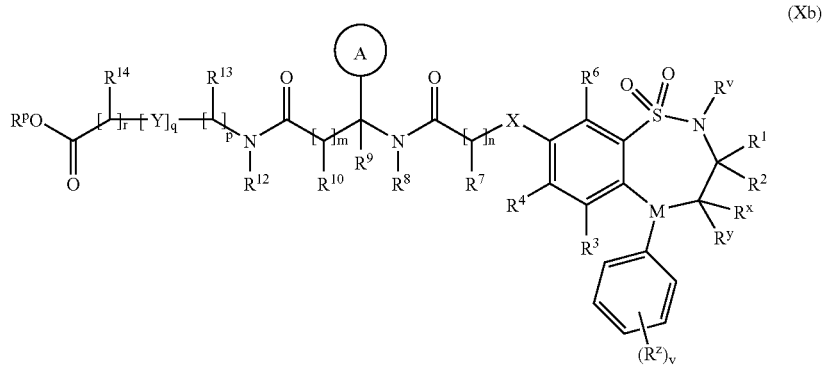

(Xb)

wherein $R^p$ together with the —OC(O)— group to which it is attached forms an ester; or Process 7): for compounds of formula (I) wherein $R^{11}$ is a group of formula (IB) and $N(R^n)C(O)$—; reacting an acid of formula (XIa):

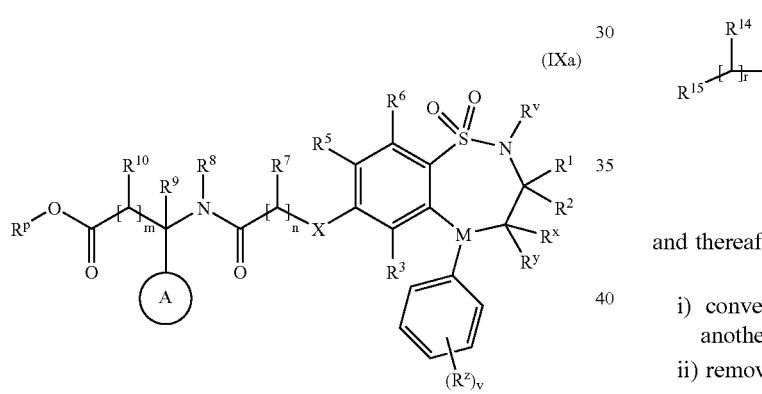

(IXa)

or (IXb):

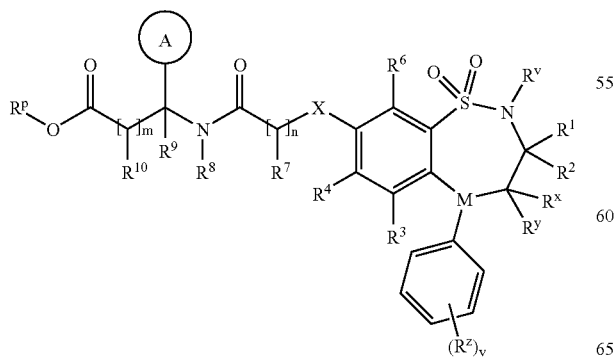

(IXb)

or an activated derivative thereof; with an amine of formula (XII):

(XII)

and thereafter if necessary or desirable:

i) converting a compound of the formula (I) into another compound of the formula (I);
ii) removing any protecting groups;
iii) forming a pharmaceutically acceptable salt.

13. A pharmaceutical composition which comprises a compound of formula (I), or a pharmaceutically acceptable salt thereof, as claimed in any one of claims 1 to 11, in association with a pharmaceutically-acceptable diluent or carrier.

14. A compound selected from the group consisting of:

1,1-dioxo-3,3-dibutyl-5-phenyl-7-methylthio-8-(N-{(R)-α-[N-((S)-1-carboxypropyl) carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine;

or a pharmaceutically acceptable salt thereof.

15. A compound selected from the group consisting of: a compound of formula (IXa):

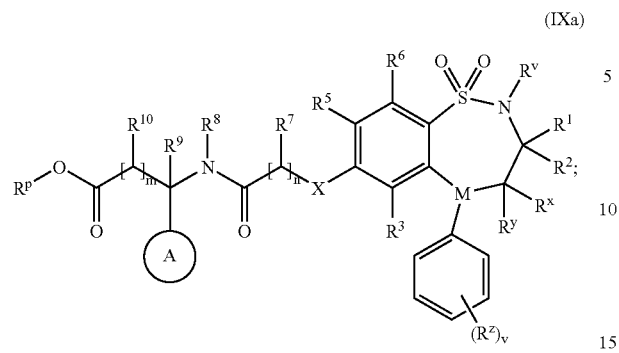
(IXa)
a compound of formula (IXb):
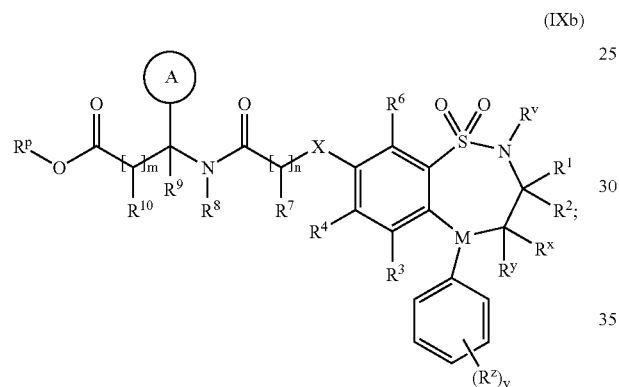
(IXb)
a compound of formula (Xa):
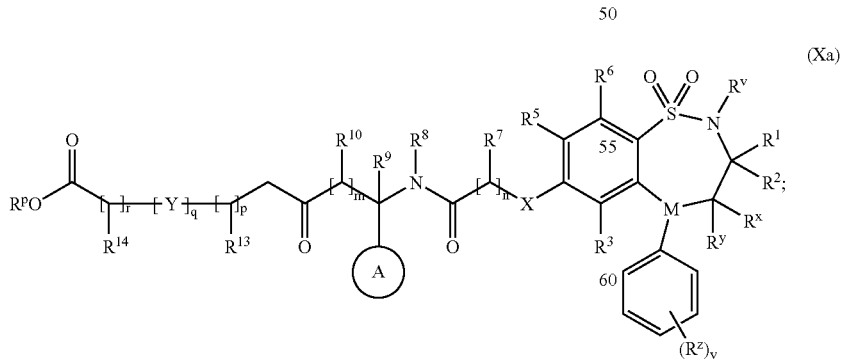
(Xa)

and a compound of formula (Xb):
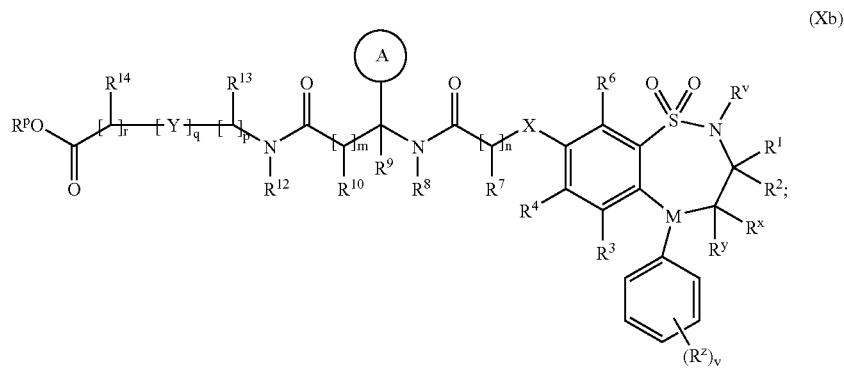
(Xb)
wherein, in each said compound, $R^v$, $R^1$, $R^2$, M, $R^x$, $R^y$, $R^z$, $R^3$, $R^4$, $R^5$, $R^6$, X, Ring A, $R^7$, $R^8$, $R^9$, $R^{10}$, $R^{11}$, Y, $R^{12}$, $R^{13}$, $R^{14}$, $R^{15}$, p, q, r, m, n, Ring B, $R^{16}$, $R^{17}$, $R^{18}$, $R^{19}$, $R^{20}$, $R^{21}$, $R^{22}$, $R^{23}$, $R^{24}$, $R^{25}$ and $R^{26}$ are as defined in claim 1, and $R^p$ is $C_{1-6}$alkyl or phenyl$C_{1-6}$alkyl;
or a pharmaceutically acceptable salt thereof.
* * * * *

UNITED STATES PATENT AND TRADEMARK OFFICE
CERTIFICATE OF CORRECTION

PATENT NO. : 7,132,416 B2
APPLICATION NO. : 10/488870
DATED : November 7, 2006
INVENTOR(S) : Ingemar Starke et al.

It is certified that error appears in the above-identified patent and that said Letters Patent is hereby corrected as shown below:

Column 68, following structures (IB) and (IC) insert

--wherein:

Y is $-N(R^n)-$, $-N(R^n)C(O)-$, $-N(R^n)C(O)(CR^sR^t)_vN(R^n)C(O)-$, $-O-$, and $-S(O)_a-$; wherein a is 0-2, v is 1-2, $R^s$ and $R^t$ are independently selected from hydrogen or $C_{1-4}$alkyl optionally substituted by $R^{26}$ and $R^n$ is hydrogen or $C_{1-4}$alkyl;

$R^{12}$ is hydrogen or $C_{1-4}$alkyl;

$R^{13}$ and $R^{14}$ are independently selected from hydrogen, $C_{1-6}$alkyl, carbocyclyl or heterocyclyl; and when q is 0, $R^{14}$ may additionally be selected from hydroxy; wherein $R^{13}$ and $R^{14}$ may be independently optionally substituted by one or more substituents selected from $R^{20}$;

$R^{15}$ is carboxy, sulpho, sulphino, phosphono, $-P(O)(OR^e)(OR^f)$, $-P(O)(OH)(OR^e)$, $-P(O)(OH)(R^e)$ or $-P(O)(OR^e)(R^f)$ wherein $R^e$ and $R^f$ are independently selected from $C_{1-6}$alkyl;

p is 1-3; wherein the values of $R^{13}$ may be the same or different;

q is 0-1;

r is 0-3; wherein the values of $R^{14}$ may be the same or different;

m is 0-2; wherein the values of $R^{10}$ may be the same or different;

n is 1-3; wherein the values of $R^7$ may be the same or different;

Ring B is a nitrogen linked heterocyclyl substituted on carbon by one group selected from $R^{23}$, and optionally additionally substituted on carbon by one or more $R^{24}$; and wherein if said nitrogen linked heterocyclyl contains an -NH- moiety, that nitrogen may be optionally substituted by a group selected from $R^{25}$;

Signed and Sealed this
Twenty-fourth Day of April, 2012

David J. Kappos
*Director of the United States Patent and Trademark Office*

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{16}$, $R^{17}$, and $R^{18}$ may be independently optionally substituted on carbon by one or more $R^{21}$;--